(12) United States Patent
Demirci et al.

(10) Patent No.: US 10,208,282 B2
(45) Date of Patent: Feb. 19, 2019

(54) SYSTEM AND METHOD FOR MAGNETIC SELF-ASSEMBLY

(71) Applicant: BRIGHAM AND WOMEN'S HOSPITAL, INC., Boston, MA (US)

(72) Inventors: Utkan Demirci, Stanford, CA (US); Savas Tasoglu, Storrs, CT (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 70 days.

(21) Appl. No.: 15/121,635

(22) PCT Filed: Feb. 25, 2015

(86) PCT No.: PCT/US2015/017451
§ 371 (c)(1),
(2) Date: Aug. 25, 2016

(87) PCT Pub. No.: WO2015/130745
PCT Pub. Date: Sep. 3, 2015

(65) Prior Publication Data
US 2016/0362655 A1     Dec. 15, 2016

Related U.S. Application Data

(60) Provisional application No. 61/944,787, filed on Feb. 26, 2014, provisional application No. 62/032,130, filed on Aug. 1, 2014.

(51) Int. Cl.
| | | |
|---|---|---|
| *C12M 1/26* | (2006.01) | |
| *C12M 1/42* | (2006.01) | |
| *C12N 5/00* | (2006.01) | |
| *C12N 13/00* | (2006.01) | |

(52) U.S. Cl.
CPC .......... *C12N 5/0062* (2013.01); *C12M 33/00* (2013.01); *C12M 35/06* (2013.01); *C12N 13/00* (2013.01); *C12N 2500/38* (2013.01); *C12N 2513/00* (2013.01); *C12N 2529/00* (2013.01); *C12N 2533/30* (2013.01); *C12N 2537/10* (2013.01)

(58) Field of Classification Search
CPC ....... C12M 33/00; C12M 35/06; C12N 13/00; C12N 2500/38; C12N 2513/00; C12N 2529/00; C12N 2533/30; C12N 2537/10; C12N 5/0062
See application file for complete search history.

(56) References Cited

U.S. PATENT DOCUMENTS

| | | |
|---|---|---|
| 7,713,923 B2 | 5/2010 | Genove et al. |
| 8,034,245 B1 | 10/2011 | Snezhko et al. |
| 2007/0049696 A1 | 3/2007 | Gonzalez Montiel et al. |
| 2011/0286975 A1 | 11/2011 | Souza et al. |
| 2012/0214217 A1 | 8/2012 | Grogan et al. |

FOREIGN PATENT DOCUMENTS

| | | |
|---|---|---|
| WO | 2008127295 A2 | 10/2008 |
| WO | 2011038370 A1 | 3/2011 |
| WO | 2013188725 A1 | 12/2013 |

OTHER PUBLICATIONS

Ames, et al., Oxidants, Antioxidants, and the Degenerative Diseases of Aging, Proc. Natl. Acad. Sci. USA, 1993, 90:7915-7922.
Birgersdotter, et al., Gene Expression Perturbation In Vitro—A Growing Case for Three-Dimensional (3D) Culture Systems, Seminars in Cancer Biology, 2005, 15:405-412.
Chaudhary, et al., Reconfigurable Assemblies of Janus Rods in AC Electric Fields, Soft Matter, 2014, 10:1320-1324.
Chung, et al., Guided and Fluidic Self-Assembly of Microstructures Using Railed Microfluidic Channels, Nature Materials, 2008, 7:581-587.
Davenport, What Controls Organ Regeneration, Science, 2005, 309:84.
Dendukuri, et al., Synthesis and Self-Assembly of Amphiphilic Polymeric Microparticles, Langmuir, 2007, 23:4669-4674.
Durmus, et al., Bioprinting: Functional Droplet Networks, Nature Materials, 2013, 12:478-479.
Fraley, et al., A Distinctive Role for Focal Adhesion Proteins in Three-Dimensional Cell Motility, Nature Cell Biology, 2010, 12(6):598-604.
Friedl, et al., Tumour-Cell Invasion and Migration: Diversity and Escape Mechanisms, Nature Reviews Cancer, 2003, 3:362-374.
Gracias, et al., Forming Electrical Networks in Three Dimensions by Self-Assembly, Science, 2000, 289:1170-1172.
Griffith, et al., Capturing Complex 3D Tissue Physiology In Vitro, Nature Reviews Molecular Cell Biology, 2006, 7:211-224.
Gurkan, et al., Emerging Technologies for Assembly of Microscale Hydrogels, Adv. Healthc. Mater., 2012, 1(2):149-158.
Hicks, What's New in Stable Radical Chemistry?, Organic & Biomoleuclar Chemistry, 2007, 5:1321-1338.
Hicks, Switchable Materials: A New Spin on Bistability, Nature Chemistry, 2011, 3:189-191.
Huang, et al., Directed Assembly of One-Dimensional Nanostructures into Functional Networks, Science, 2001, 291:630-633.
Hulteen, et al., Nanosphere Lithography: A Materials General Fabrication Process for Periodic Particle Array Surfaces, J. Vac. Sci. Technol. A, 1995, 13(3):1553-1558.
Jacobs, et al., Fabrication of a Cylindrical Display by Patterned Assembly, Science, 2002, 296:323-325.

(Continued)

*Primary Examiner* — Deborah K Ware
(74) *Attorney, Agent, or Firm* — Quarles & Brady LLP

(57) ABSTRACT

In one aspect, the present disclosure provides a method for self-assembly of magnetic building blocks, including distributing a plurality of building blocks in a liquid medium, each of the plurality of building blocks having a plurality of stable radicals, establishing a magnetic field interacting with at least a portion of the plurality of building blocks, guiding with the magnetic field the portion of the plurality of building blocks from a first location in the liquid medium to a second location in the liquid medium, assembling into a first construct the portion of the plurality of building blocks proximate the second location, and treating the first construct with at least one antioxidant to neutralize at least in part the plurality of stable radicals.

20 Claims, 22 Drawing Sheets

(56) References Cited

OTHER PUBLICATIONS

Jain, et al., High-Temperature Metal-Organic Magnets, Nature, 2007, 445:291-294.
Langer, et al., Tissue Engineering, Science, 1993, 260(5110):920-926.
Langer, et al., Designing Materials for Biology and Medicine, Nature, 2004, 428:487-492.
Lee, et al., Three-Dimensional Micropatterning of Bioactive Hydrogels Via Two-Photon Laser Scanning Photolithography for Guided 3D Cell Migration, Biomaterials, 2008, 29(20):2962-2968.
Lu, et al., A Self-Assembly Approach to the Fabrication of Patterned, Two-Dimensional Arrays of Microlenses of Organic Polymers, Advanced Materials, 2001, 13(1):34-37.
Luo, et al., A Photolabile Hydrogel for Guided Three-Dimensional Cell Growth and Migration, Nature Materials, 2004, 3:249-253.
Mas-Torrent, et al., Attaching Persistent Organic Free Radicals to Surfaces: How and Why, Chemical Reviews, 2012, 112:2506-2527.
Mirica, et al., Using Magnetic Levitation for Three Dimensional Self-Assembly, Advanced Materials, 2011, 23:4134-4140.
Ormonde, et al., Nanosphere Lithography: Fabrication of Large-Area Ag Nanoparticle Arrays by Convective Self-Assembly and Their Characterization by Scanning UV-Visible Extinction Spectroscopy, Langmuir, 2004, 20:6927-6931.
Park, et al., Microporous Cell-Laden Hydrogels for Engineered Tissue Constructs, Biotechnol. Bioeng., 2010, 106(1):138-148.
Rizvi, et al., Flow Induces Epithelial-Mesenchymal Transition, Cellular Heterogeneity and Biomarker Modulation in 3D Ovarian Cancer Nodules, PNAS, 2013, 110:E1974-E1983.
Rothemund, Folding DNA to Create Nanoscale Shapes and Patterns, Nature, 2006, 440:297-302.
Salalha, et al., Investigation of Fluidic Assembly of Nanowires Using a Droplet Inside Microchannels, Physics of Fluids, 2005, 17:063301-1 thru 063301-5.
Scott, et al., High-Performance Inductors Using Capillary Based Fluidic Self-Assembly, Journal of Microelectromechanical Systems, 2004, 13(2):300-309.
Srinivasan, et al., Microstructure to Substrate Self-Assembly Using Capillary Forces, Journal of Microelectromechanical Systems, 2001, 10(1):17-24.
Stauth, et al., Self-Assembled Single-Crystal Silicon Circuits on Plastic, PNAS, 2006, 103(38):13922-13927.
Subramaniam, et al., Noncontact Orientation of Objects in Three-Dimensional Space Using Magnetic Levitation, PNAS, 2014, 111(36):12980-12985.
Tanase, et al., Magnetic Trapping and Self-Assembly of Multicomponent Nanowires, Journal of Applied Physics, 2002, 91:8549-8551.
Tasoglu, et al., Manipulating Biological Agents and Cells in Micro-Scale Volumes for Applications in Medicine, Chem. Soc. Rev., 2013, 42(13):5788-5808.
Tasoglu, et al., Guided and Magnetic Self-Assembly of Tunable Magnetoceptive Gels, Nature Communciations, 2014, 5, Article No. 4702.
Tasoglu, et al., Untethered Micro-Robotic Coding of Three-Dimensional Material Composition, Nature Communications, 2014, 5:3124.
Tasoglu, et al., Bioprinting for Stem Cell Research, Trends in Biotechnology, 2013, 31(1):10-19.
Tasoglu, et al., Paramagnetic Levitational Assembly of Hydrogels, Advanced Materials, 2013, 25:1137-1143.
Tibbitt, et al., Hydrogels as Extracellular Matrix Mimics for 3D Cell Culture, Biotechnol. Bioeng., 2009, 103(4):655-663.
Whitesides, et al., Self-Assembly at All Scales, Science, 2002, 295:2418-2421.
Xia, et al., Template-Assisted Self-Assembly of Spherical Colloids Into Complex and Controllable Structures, Advanced Functional Materials, 2003, 13(12):907-918.
Xu, et al., Three-Dimensional Magnetic Assembly of Microscale Hydrogels, Advanced Materials, 2011, 23:4254-4260.
Xu, et al., Release of Magnetic Nanoparticles from Cell-Encapsulating Biodegradable Nanobiomaterials, ACS Nano, 2012, 6:6640-6649.
Yan, et al., Linking Synchronization to Self-Assembly Using Magnetic Janus Colloids, Nature, 2012, 491:578-581.
Yan, et al., Colloidal Ribbons and Rings from Janus Magnetic Rods, Nature Communications, 2013, 4:1516, 9 pp.
Zaman, et al., Migration of Tumor Cells in 3D Matrices is Governed by Matrix Stiffness Along with Cell-Matrix Adhesion and Proteolysis, PNAS, 2006, 103(29):10889-10894.
PCT International Search Report and Written Opinion, PCT/US2015/017451, dated May 27, 2015.
Intellectual Property Office of Singapore, Written Opinion, Application No. 11201607101V, dated Aug. 3, 2017, 5 pages.
Shapiro, et al., Magnetic Levitation as a Platform for Competitive Protein-Ligand Binding Assays, Analytical Chemistry, 2012, 84:6166-6172.
Tseng, et al., Assembly of a Three-Dimensional Multitype Bronchiole Coculture Model Using Magnetic Levitation, Tissue Engineering: Part C, 2013, 19(9):1-11.
European Patent Office, Extended European Search Report, Application No. 15755490.8, dated Sep. 21, 2017, 8 pages.
Intellectual Property Office of Singapore, Examination Report, Application No. 11201607101V, dated Jan. 9, 2018, 4 pages.

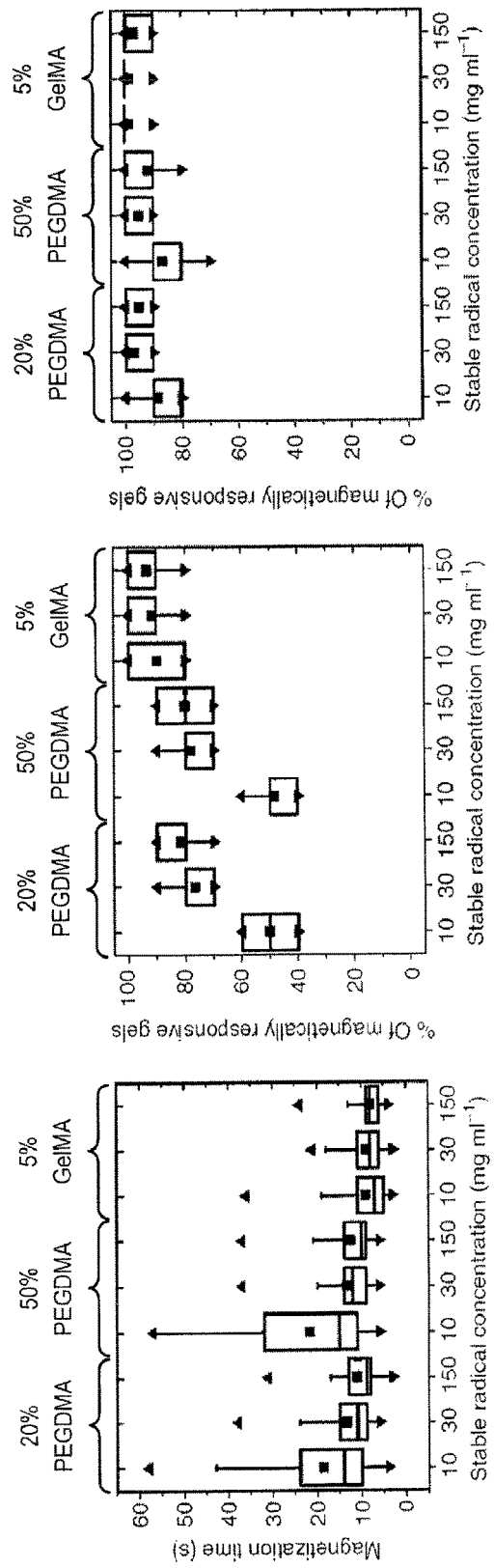

SYSTEM AND METHOD FOR MAGNETIC SELF-ASSEMBLY

CROSS-REFERENCE TO RELATED APPLICATIONS

This application represents the U.S. national stage of PCT International Application No. PCT/US2015/017451 filed Feb. 26, 2015, which claims priority to U.S. Provisional Patent Application No. 61/944,787 filed on Feb. 26, 2014 and U.S. Provisional Patent Application Ser. No. 62/032,130 filed on Aug. 1, 2014. The contents of all of these applications are incorporated herein by reference in their entirety for all purposes.

STATEMENT REGARDING FEDERALLY SPONSORED RESEARCH

This invention was made with government support under CAREER Award Number 1150733 awarded by the National Science Foundation, and under R01EB015776-01A1, R15HL115556, and R21HL112114 awarded by the National Institutes of Health. The government has certain rights in the invention.

BACKGROUND OF THE INVENTION

The disclosure relates, in general, to self-assembly of building blocks and, more particularly, a system and method for guided self-assembly of magnetic building blocks including stable radicals.

Self-assembly is a promising and non-invasive strategy for parallel fabrication of heterogeneous functional systems made of various microstructures. Several self-assembly studies utilizing principles such as fluidic force, surface energy, magnetic force, gravity, electrostatic force, or capillary force have been presented for multiple applications. These self-assembly methods are often massively parallel, and thus, less expensive and faster than deterministic methods such as robotic assembly. However, assembly precision and yield are not as high as serial pick-and-place assembly owing to the probabilistic nature of self-assembly. To increase the yield of the assembly, excessive numbers of components were used within the assembly regions. Therefore, redundant mass fabrication of microstructures is required in most fluidic self-assembly methods, and there is an unmet need to develop efficient and inexpensive self-assembly methods merging the advantages of high-yield deterministic assembly and high-throughput self-assembly.

In general, microcomponent manipulation strategies using magnetism are versatile, contactless and inexpensive. In most of these strategies, magnetic micrometer-scale or nanometer-scale beads are used. Commercial magnetic beads are made of mainly iron oxide with minor amounts of other elements such as nickel and cobalt encapsulated in a polymer shell. Because of the risk of heavy metal poisoning, use and release of such magnetic beads in clinical applications have to be proven.

Therefore, there is a need for development of alternative beads that are potentially heavy metal-free for biological applications.

SUMMARY OF THE INVENTION

The present invention overcomes the aforementioned drawbacks by providing a system and method for self-assembly of magnetic building blocks. According to one embodiment of the present disclosure, a method for self-assembly of magnetic building blocks includes, distributing a plurality of building blocks in a liquid medium, each of the plurality of building blocks including a plurality of stable radicals, establishing a magnetic field interacting with at least a portion of the plurality of building blocks, guiding with the magnetic field the portion of the plurality of building blocks from a first location in the liquid medium to a second location in the liquid medium, assembling into a first construct the portion of the plurality of building blocks proximate the second location, and treating the first construct with at least one antioxidant to neutralize at least in part the plurality of stable radicals.

In one aspect, the method includes incubating the plurality of building blocks in a composition including the plurality of stable radicals.

In another aspect, the step of assembling into the construct the portion of the plurality of building blocks further includes cross-linking together each of the building blocks that comprise the first construct. For example, following self-assembly of the building blocks, a composition including a cross-linkable polymer may be coated onto the building blocks forming the assembled construct. Thereafter, the polymer may be cross-linked together, thereby forming cross-links between building blocks and stabilizing the assembled construct.

In yet another aspect, the plurality of building blocks includes at least one of nucleic acids, proteins, cells, and tissues. The nucleic acids, proteins, cells, or tissues may be coated on or incorporated into the building blocks.

In a further aspect, the plurality of building blocks is essentially free of iron, nickel, and cobalt. In one example, the plurality of building blocks may be considered to be essentially free of iron, nickel, and cobalt if the plurality contains less than about 100 parts per million (ppm) of iron, nickel, and cobalt. In another example, the plurality of building blocks may be considered to be essentially free of iron, nickel, and cobalt if the plurality contains less than about 1 ppm of iron, nickel, and cobalt. In yet another example, the plurality of building blocks may be considered to be essentially free of iron, nickel, and cobalt if the plurality contains less than about 1 part per billion (ppb) of iron, nickel, and cobalt.

In still another aspect, the density of each of the plurality of building blocks is less than the density of the liquid medium such that the plurality of building blocks floats on a surface of the liquid medium.

In one aspect, the plurality of building blocks includes at least a first fraction of building blocks having a first density and a second fraction of building blocks having a second density different from the first density such that there is a differential in buoyancy between the first fraction and the second fraction.

In another aspect, the method further includes submerging the first construct in a first liquid phase, forming a second liquid phase on top of the first liquid phase, assembling a second construct including at least a second portion of the plurality of building blocks, the second construct assembled in the second liquid phase relatively above the first construct, and displacing at least one of the first liquid phase and the second liquid phase, thereby layering the second construct on the first construct to form a three dimensional structure.

In yet another aspect, the liquid medium includes a surfactant to decrease the surface tension and drag forces on the plurality of building blocks.

In a further aspect, the plurality of building blocks including the plurality of stable radicals is paramagnetic.

According to another embodiment of the present disclosure, a system for self-assembly of magnetic building blocks includes a liquid medium, a reservoir for containing the liquid medium, a plurality of building blocks for distribution in the liquid medium, each of the plurality of building blocks including a plurality of stable radicals, a magnetic field established relative to the reservoir, the magnetic field interacting with at least a portion plurality of building blocks when the plurality of building blocks are distributed in the liquid medium, the magnetic field operable to guide the portion of the plurality of building blocks from a first location in the liquid medium to a second location in the liquid medium and assemble into a first construct the portion of the plurality of building blocks proximate the second location, and a composition including an antioxidant for treating the first construct to neutralize at least in part the plurality of stable radicals.

In one aspect, the liquid medium includes a surfactant to decrease the surface tension and drag forces on the plurality of building blocks.

In another aspect, the plurality of building blocks includes at least one of nucleic acids, proteins, cells, and tissues.

In yet another aspect, the plurality of building blocks is essentially free of iron, nickel, and cobalt.

In a further aspect, the density of each of the plurality of building blocks is less than the density of the liquid medium such that the plurality of building blocks floats on a surface of the liquid medium.

In one aspect, the plurality of building blocks includes at least a first fraction of building blocks having a first density and a second fraction of building blocks having a second density different from the first density such that there is a differential in buoyancy between the first fraction and the second fraction.

In another aspect, the system further includes a permanent magnet for establishing the magnetic field.

In yet another aspect, the plurality of building blocks including the plurality of stable radicals is paramagnetic.

In a further aspect, the system further includes at least one ultraviolet light source for cross-linking the portion of the plurality of building blocks that comprises the first construct.

According to yet another embodiment of the present disclosure, a method for self-assembly of magnetic building blocks includes incubating a plurality of building blocks in a composition including a plurality of stable radicals, distributing the plurality of building blocks in a reservoir containing a liquid medium, establishing a magnetic field with a permanent magnet, the magnetic field encompassing at least a portion of the plurality of building blocks, guiding with the magnetic field the portion of the plurality of building blocks from a first location in the liquid medium to a second location in the liquid medium, assembling into a first construct the portion of the plurality of building blocks proximate the second location, cross-linking the portion of the plurality of building blocks that comprises the first construct, and treating the first construct with at least one antioxidant to neutralize at least in part the plurality of stable radicals. The density of each of the plurality of building blocks is less than the density of the liquid medium such that the plurality of building blocks floats on a surface of the liquid medium.

According to yet another embodiment of the present disclosure, a method for self-assembly of building blocks includes distributing a plurality of building blocks in a paramagnetic liquid medium, establishing a magnetic field interacting with the paramagnetic liquid medium, guiding with the magnetic field the portion of the plurality of building blocks from a first location in the liquid medium to a second location in the paramagnetic liquid medium, and assembling into a first construct the portion of the plurality of building blocks proximate the second location.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 3A is a plot of magnetization time as a function of stable radical concentration for hydrogel building blocks soaked in a solution including 10, 30, or 150 mg ml$^{-1}$ 4-amino-TEMPO stable radical in PBS for 30 min.

FIG. 3B is a plot of the fraction (%) of hydrogel building blocks that were magnetically responsive within 15 seconds of initial exposure to a magnetic field as a function of stable radical concentration for hydrogel building blocks soaked in a solution including 10, 30, or 150 mg ml$^{-1}$ 4-amino-TEMPO stable radical in PBS for 30 min.

FIG. 3C is a plot of the fraction (%) of hydrogel building blocks that were magnetically responsive within 1 minute of initial exposure to a magnetic field as a function of stable radical concentration for hydrogel building blocks soaked in a solution including 10, 30, or 150 mg ml$^{-1}$ 4-amino-TEMPO stable radical in PBS for 30 min.

FIG. 6A is a heat map for a simulation of magnetic field norm (contour) and flux density (arrows) created by two magnets in anti-Helmholtz configuration for.

DETAILED DESCRIPTION OF THE INVENTION

Figure 1A:
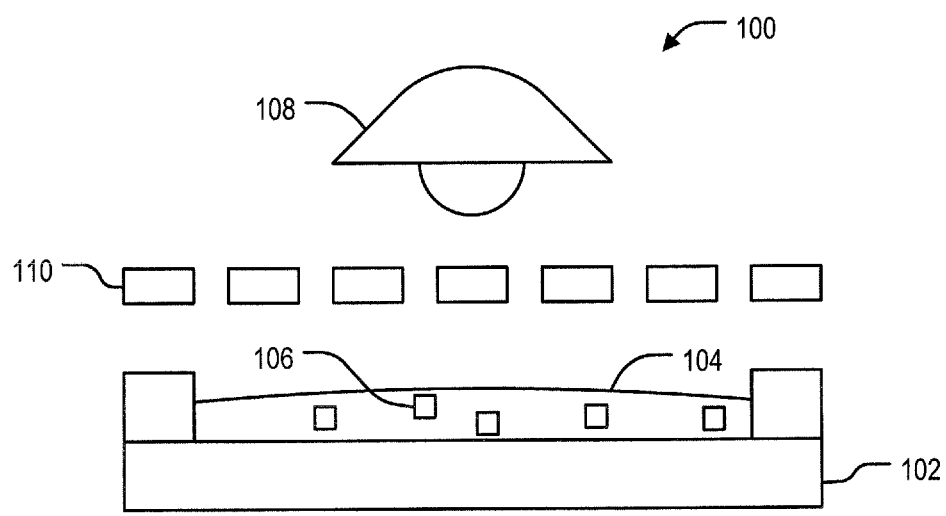
FIG. 1A is a schematic illustration of an example system for the microfabrication of cell encapsulating hydrogels via UV photocross-linking. 50 µl of gel precursor solution was pipetted onto a glass slide and then exposed to UV light (500 mW; at a height of 50 mm above the gels) for 20 seconds. Several types of photomasks with different patterns were employed.

As also discussed above, in various situations it may be useful to provide a system and method for the self-assembly of various components. In one aspect, self-assembly processes may produce both simple and complex functional patterns over a range of length scales. For example, self-assembly processes that produce micro-scale patterns are common in nature. These processes have been reproduced in the laboratory for use in diverse fields such as optoelectronics, microfabrication, sensors, tissue engineering, computation, and the like. However, many self-assembly processes include components that may not be compatible with biological systems. In one example, beads or other materials for magnetic manipulation and assembly may include one or more heavy metals. These heavy metals may be known to be incompatible with living tissues or organisms. Alternatively (or in addition), the effect of the heavy metals on a biological system may be unknown or unpredictable, thereby implicating extensive clinical testing, which may delay or prevent the implementation of a system and method including the heavy metal materials. Various other challenges may arise as additional factors are taken into account.

Use of the disclosed system and method for magnetic self-assembly may address these and other issues. In one embodiment, stable radicals may be used to guide the self-assembly of magnetically tunable gels or other magnetoceptive materials. Herein, the term "magnetoceptive" refers to any magnetically responsive material or component that may be programmed by shape and composition, into heterogeneous complex structures. Magnetoceptive materials may include structures having dimensions on the order of about 100 micrometers ($\mu$m) to about 1 millimeter (mm). However, in some embodiments, magnetoceptive material may include structures having dimensions on the order of about 1 $\mu$m to about 1 cm.

A system and method according to the present disclosure may exploit the paramagnetism of free radicals as a driving mechanism for the assembly of simple, complex, homogeneous, and heterogeneous structures. In one aspect, the structures may be assembled in the presence of a magnetic field generated by permanent magnets, electromagnets, temporary magnets, or a combination thereof. In some embodiments, the overall magnetic signature of final structure may be subsequently reduced or eliminated through exposure to an antioxidant such as vitamin E. Embodiments of the present disclosure may facilitate fabrication of soft systems with heterogeneity in material properties (e.g., porosity, elastic modulus, and mass density), bottom-up tissue engineering, levitational and selective assembly of microcomponents, and the like.

In vivo, cells in functional units may be embedded in a three dimensions (3D) microenvironment including extracellular matrix and neighboring cells with a defined spatial distribution. Tissue functionality may arise from these components and may be influenced by their relative spatial locations. As compared with cells in native tissues and in 3D culture conditions, cells cultured in two dimensional (2D) monolayers may display significant differences in gene expression profiles. Hence, 2D systems may not effectively represent the complex 3D tissue environment. Accordingly, the present disclosure may provide a system and method for magnetic self-assembly of 3D structures for cell culture. In one embodiment, magnetically tunable microcomponents including stable radicals may be self-assembled with the aid of an external magnetic field. The magnetic sensitivity of the stable radicals may be quenched (i.e., reduced or eliminated) through exposure to the antioxidant vitamin E. The approach may be used to guide self-assembly of complex constructs in 3D with unique heterogeneous material properties such as porosity, elastic modulus, and mass density.

In some embodiments, the present disclosure provides hydrogels and other magnetoceptive materials that are responsive to a magnetic field (magnetically active) for a time period of at least about 2 weeks. The magnetoceptive nature of the materials may be controlled through the use of an antioxidant treatment when magnetization is no longer needed. The resulting materials or assembled structures may be free of magnetic particles as compared with other systems where magnetic nanoparticles (MNP) need to be eliminated by physical release mechanisms (e.g., through the kidney of an organism) for clinical applications. Further, magnetically active stable radicals may be used to change the magnetic signature of a microenvironment to selectively levitate a magnetoceptive material and guide 3D self-assembly of micro-scale objects.

The principles that underlie the fabrication of magnetoceptive materials, and guided self-assembly of these components into various structures may be further understood with reference to the Figures as well as with reference to Tasoglu, S. et al., *Nat. Commun.* 5:4702 (2014).

Figure 1B:
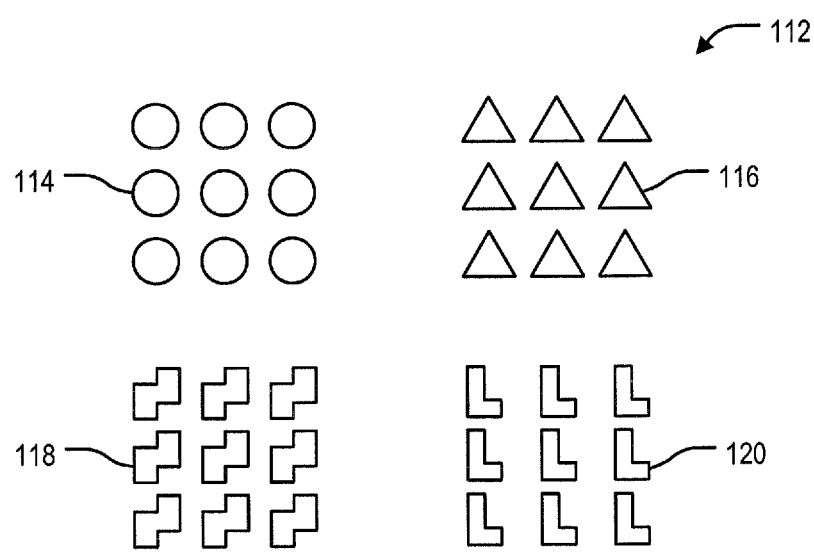
FIG. 1B is a schematic illustration showing a plan view of four example groups of building blocks including circular (top left), triangular (top right), zig-zag shaped (bottom left) and L-shaped (bottom right) building blocks.

Turning now to a first embodiment illustrated in FIGS. 1A-1D, a system 100 for preparing building blocks for assembly into various structures may includes a stage 102 for supporting a composition 104. The composition 104 may be initially provided as a liquid solution including one or more cross-linkable polymers such as methacrylated gelatin (GelMA), polyethylene glycol dimethacrylate (PEGDMA), or the like. Cross-linking of the polymers may be carried out through the application of light or heat, the addition of one or more chemicals, or the like. Further, the composition 104 may include one or more additional components 106 such as cells, magnetic particles, growth factors, media components, the like, or combinations thereof. The system 100 may be used to cross-link at least a portion of the composition 104 using an ultraviolet (UV) light source 108 and one or more patterned masks 110 to provide a plurality of microgels or building blocks 112 having dimensions on the order of about 100 $\mu$m to about 100 mm (FIG. 1B). It will be appreciated that building blocks 112 may be provided in a variety of shapes and sizes by varying the design of the masks 110. Example profiles of building blocks 112 that may be achieved include circles 114, triangles 116, skew-tetrominoes 118, and L-tetrominoes 120. Generally, the building blocks 112 illustrated in FIG. 1B may be three-dimensional prisms with circles 114 corresponding with cylinder-shaped building blocks 112, triangles 116 corresponding with triangular prism-shaped building blocks 112, and so forth.

Figure 1C:
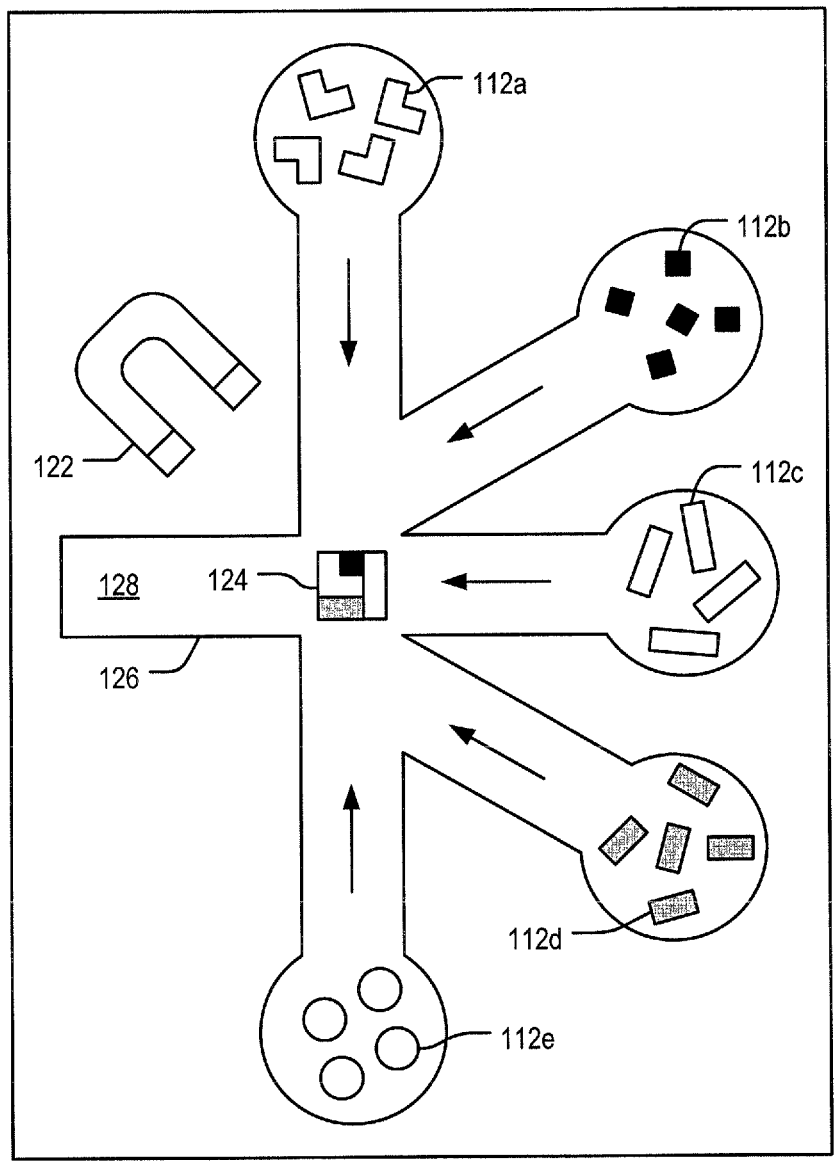
FIG. 1C is a schematic illustration of an example system for guided paramagnetic self-assembly of hydrogel building blocks using a permanent NdFeB magnet on a liquid reservoir composed of OptiPrep (20-30 (v/v) %) and Tween-80 (0.001 (v/v) %) in Dulbecco's Phosphate-Buffered Saline (DPBS). Following assembly, a minute amount of precursor solution is ejected onto the assembly. Secondary UV cross-linking was performed to stabilize the overall shape. Vitamin E treatment was applied to switch off the magnetism of assembled hydrogels, which in turn increases the viability of cells that are encapsulated into hydrogels.

In one aspect, building blocks 112 may undergo paramagnetization or radicalization by submerging, soaking, or incubating the building blocks 112 in a solution including one or more stable radicals. One example class of a stable radical includes 4-Amino-2,2,6,6-tetramethylpiperidine-1-oxyl (4-Amino-TEMPO) and derivatives thereof. Other example classes of stable radicals include DOXYL radicals such as 2-(3-Carboxypropyl)-4,4-dimethyl-2-tridecyl-3-oxazolidinyloxy (5-DOXYL-strearic acid), picrylhydrazyl radicals such as 2,2-Diphenyl-1-picrylhydrazyl, and the like. Thereafter, the building blocks 112 may be self-assembled with guidance of a magnet 122 (FIG. 1C). One example magnet is a permanent neodymium (NdFeB) magnet. However, other types of magnets may be used to guide the building blocks 112.

With reference to FIG. 1C, in some embodiments, self-assembly of building blocks 112 into a structure or construct 124 may be carried out in a reservoir 126. The reservoir 126 may be filled with an aqueous solution or other liquid medium 128. One example liquid medium 128 includes a density modifying agent and a surface active agent or surfactant. One example density modifying agent is an iodixanol solution such as OptiPrep™ density gradient medium manufactured by AXIS-SHIELD of Oslo, Norway. Other suitable density modifying agents may include any material or composition that increases the density of solution 128, thereby enabling building blocks 112 to float on the surface of the solution 128 in the reservoir 126. For example, upon distributing a plurality of building blocks 112 in the liquid medium 128, each of the plurality of building blocks 112 may float on or at a surface of the liquid medium 128. In one aspect, the surface may be an interface of the liquid medium with air, another gas composition, or another liquid composition such as mineral oil. In another aspect, the building blocks 112 may be partially or completely submerged beneath the surface of the liquid medium 128.

Figure 1D:
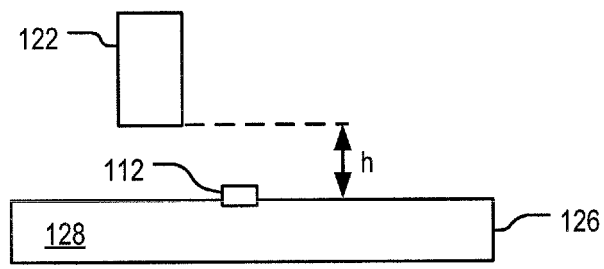
FIG. 1D is a schematic illustration of manipulation of a building block as a function of distance between the magnet and the surface of the liquid medium.
Figure 1E:
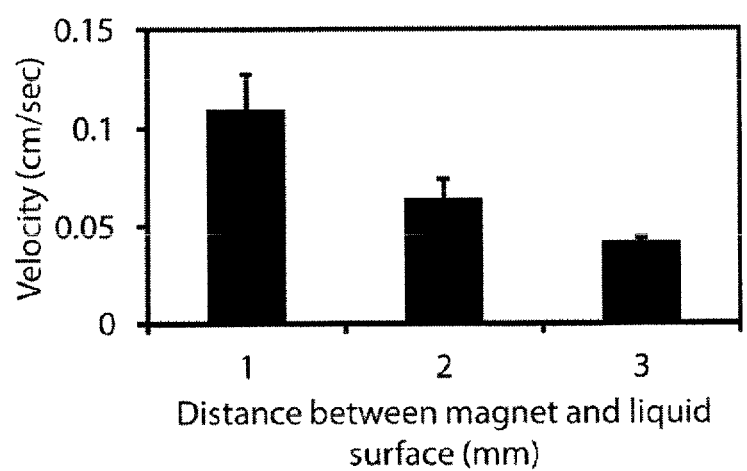
FIG. 1E is a bar graph of velocity distances of 1, 2, and 3 mm between the magnet and the surface of the liquid medium. A single PEGDMA gel was placed at 1.5 cm apart from the center of magnet. Once the magnet was fixed, the motion of the gel towards the center of the magnet was recorded. The vertical distance between magnet and gel was controlled (1 mm, 2 mm, and 3 mm). Average velocity was calculated by dividing the distance between initial and final location of the gel by the elapsed time. 200 mg ml$^{-1}$ 4-amino-TEMPO was used for gel-magnetization.

Example surface active agents include non-ionic surfactants such as polysorbate 80. Other suitable surface active agents include any anionic, cationic, non-ionic, and zwitterionic material or composition that decreases the surface tension of the solution 128 or drag forces on building blocks 112 in the solution 128. In one aspect, a solution 128 including a surface active agent may enable faster motion of the building blocks 112 in the solution 128. In one aspect, when the distance between the magnet 122 and building blocks 112 is decreased, the average velocity of building blocks 112 may increase (FIGS. 1D and 1E).

Figure 1F:
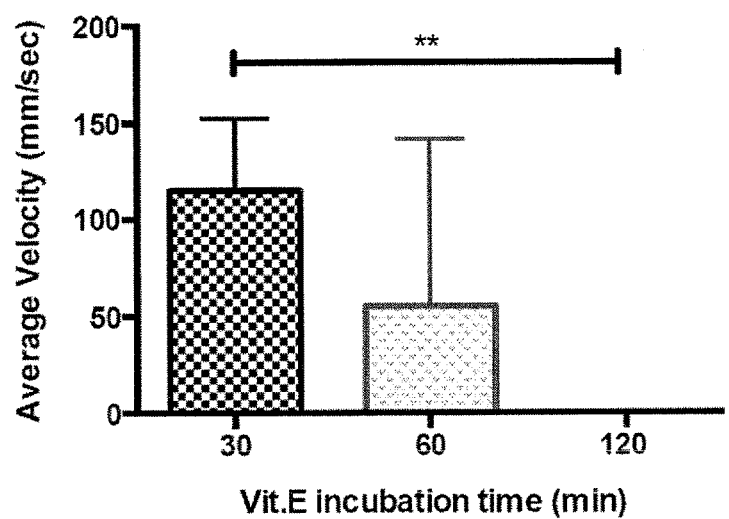
FIG. 1F is a bar graph showing average velocity of a building block for different Vitamin E incubation times. For 60 minutes of vitamin E incubation, only 2 out of 6 gels moved.

In the example illustrated in FIG. 1C, the construct 124 includes one of each of an assortment of the building blocks 112 including a group of building blocks 112a, a group of building blocks 112b, a group of building blocks 112c, a group of building blocks 112d, and a group of building blocks 112e. To stabilize the overall shape of the construct 124, secondary cross-linking may be performed following guided self-assembly of the building blocks 112 using the magnet 122. In one aspect, after assembly, it may be useful to "switch off" magnetization (i.e., demagnetize) the construct 124, minimize potential effects of free radicals on cell proliferation for tissue engineering applications, or a combination thereof. Accordingly, assembled constructs may be submerged into an antioxidant solution following the secondary cross-linking (FIGS. 1C and 1F).

Antioxidants may neutralize free radicals by accepting or donating an electron to eliminate the unpaired condition. In general, the antioxidant becomes a free radical in the process of neutralizing a free radical to a non-free radical molecule. The free radical form of the antioxidant will usually be less reactive than the free radical that was neutralized. The antioxidant molecule may be very large allowing it to distribute the charge of the unpaired electron, readily neutralized by another antioxidant, have another mechanism for terminating its free radical condition, or a combination thereof.

Free radicals may be listed by one-electron reduction potentials in milliVolts (mV). The reduced form of each radical is capable of neutralizing (reducing) free radicals having a higher potential. Hydroxyl radical (OH) has one of the highest potentials at about 2300 mV and may be the most destructive (reactive). One example antioxidant includes (+)-α-tocopherol acetate (i.e., vitamin E), which has a radical reaction potential of about 480 mV. Other example antioxidants include vitamin C (ascorbate) and glutathione, which have reaction potentials of about 282 mV and about 920 mV, respectively. In one aspect, it may be useful to use vitamin E as it is an effective antioxidant for terminating the chain reactions of lipid peroxidation in cell membranes. In other embodiments, a plurality of antioxidants, such as a combination of vitamin E, vitamin C, glutathione, gamma-tocopherol, melatonin, lycopene, and the like may be used to increase the effectiveness of an antioxidant treatment as different antioxidants may be more effective for neutralizing a given reactive oxygen species or reactive nitrogen species.

In one aspect, once the building blocks 112 are assembled, the resulting construct 124 may remain assembled due to capillary forces and, in the case of hydrogel building blocks or the like, the stickiness of the building blocks 112. Further, after assembly, secondary cross-linking may be performed to stabilize the geometry of the construct 124. Antioxidant treatment may be performed following secondary cross-linking and stabilization of assembled gels. Therefore, the antioxidant treatment may not affect the geometry of the assembled construct 124.

Figure 1G:
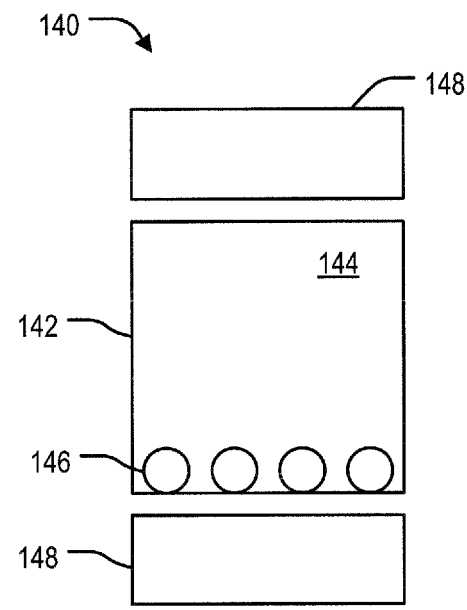
FIGS. 1G and 1H are schematic illustrations of an elevational view of an example system for levitational self-assembly of hydrogels in radical solution using two permanent NdFeB magnets in anti-Helmholtz configuration (that is, a configuration in which the same poles face each other). Positive difference between magnetic susceptibilities of radical solution ($\chi_{medium}$) medium) and gels ($\chi_{object}$) leads to levitational assembly of gels.
Figure 1H:
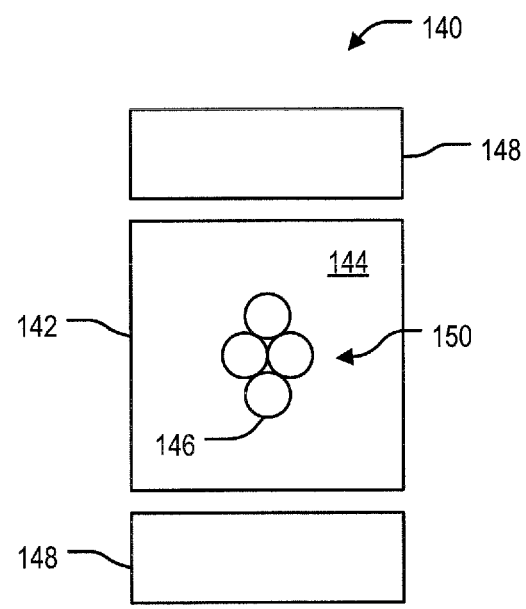

In another example, stable radicals may be utilized to modify the magnetic susceptibility of a suspension liquid and to guide levitational self-assembly of beads, hydrogels, or other like building blocks. With reference to FIGS. 1G and 1H, a system 140 for levitational self-assembly may include a container 142 filled with a medium 144. A plurality of building blocks 146 may be added to the container 142. In one aspect, the medium 144, the building blocks 146, or a combination thereof may include one or more magnetically responsive components. For example, it may be useful to provide a medium 144 including one or more stable radicals, gadolinium ions ($Gd^{3+}$), manganese ions ($Mn^{2+}$), the like, or combinations thereof. In the case that the medium 144 includes a magnetically responsive component, it may be useful to provide building blocks 146 that are untreated or substantially free of stable radicals or other magnetically responsive materials.

Turning to FIG. 1G, the building blocks 146 may have a density that is greater than the medium 144 and therefore may initially rest at the bottom of the container 142. The system 140 may further include a pair of magnets 148 arranged in an anti-Helmholtz configuration. Upon application or activation of the magnets, the building blocks 146 may be levitated in a controlled manner, thereby resulting in self-assembly of the building blocks 146 into a construct 150.

Figure 2A:
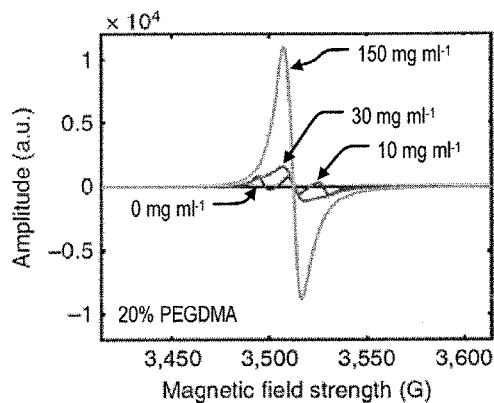
FIG. 2A is an Electron Paramagnetic Resonance (EPR) spectra showing amplitude as a function of magnetic field strength for 20% PEGDMA building blocks soaked in a solution including 0, 10, 30, or 150 mg ml$^{-1}$ 4-amino-TEMPO stable radical in PBS for 10-15 h. Building blocks were cylinders having a diameter of 3 mm and a height of 1.5 mm.
Figure 2B:
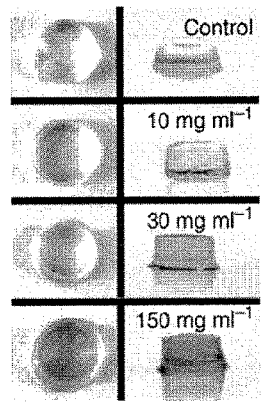
FIG. 2B is an image of the building blocks analyzed in FIG. 2A. Building blocks showed a color change depending on radical concentration.
Figure 2C:
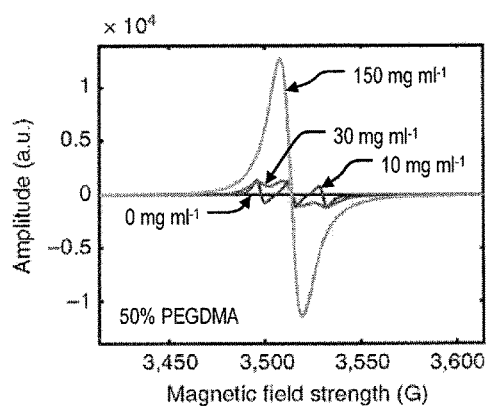
FIG. 2C is an EPR spectra showing amplitude as a function of magnetic field strength for 50% PEGDMA building blocks soaked in a solution including 0, 10, 30, or 150 mg ml$^{-1}$ 4-amino-TEMPO stable radical in PBS for 10-15 h. Building blocks were cylinders having a diameter of 3 mm and a height of 1.5 mm.
Figure 2D:
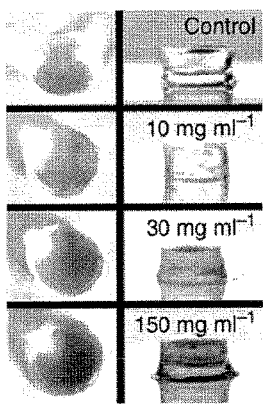
FIG. 2D is an image of the building blocks analyzed in FIG. 2C. Building blocks showed a color change depending on radical concentration.
Figure 2E:
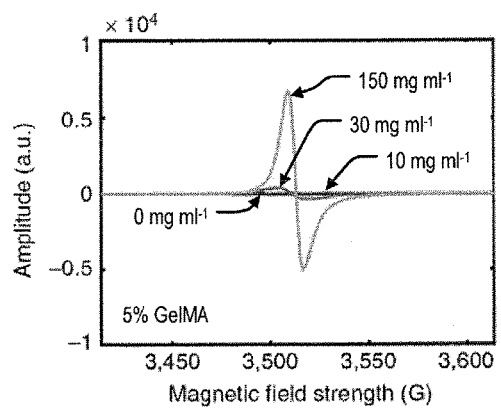
FIG. 2E is an EPR spectra showing amplitude as a function of magnetic field strength for 5% GelMA building blocks soaked in a solution including 0, 10, 30, or 150 mg ml$^{-1}$ 4-amino-TEMPO stable radical in PBS for 10-15 h. Building blocks were cylinders having a diameter of 3 mm and a height of 1.5 mm.
Figure 2F:
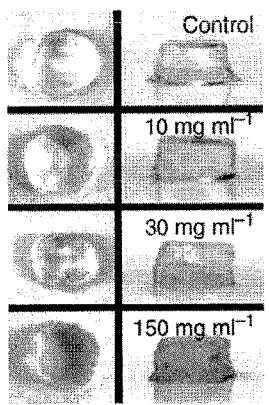
FIG. 2F is an image of the building blocks analyzed in FIG. 2E. Building blocks showed a color change depending on radical concentration.

To characterize the magnetization of hydrogels, electron paramagnetic resonance (EPR) measurements may be performed. With reference to FIGS. 2A-2I, cylindrical building blocks were prepared comprising 20% (w/v) PEGDMA hydrogels. The building blocks were then incubated (soaked) in either a solution of phosphate-buffered saline (PBS), or a stable radical solution including either 10, 30, or 150 mg $ml^{-1}$ of a stable radical solution. In one aspect, EPR intensity or spin density may provide an indication of an absorbed amount of radicals in the hydrogel building blocks. With reference to FIGS. 2A and 2B, as the concentration of the stable radical solution increased, EPR intensity or spin density increased as well. To show versatility of paramagnetization of hydrogels, EPR measurements were performed for 50% PEGDMA and 5% GelMA (see FIGS. 2C-2F). Results showed that of the samples tested, 50% PEGDMA gels have the largest spin density indicating the highest absorbed amount of radicals. As shown in FIGS. 2B, 2D, and 2F, soaked hydrogels showed a noticeable color change that corresponded with the concentration of stable radicals. Further, EPR spectra of all building blocks showed an increase in spin density as the radical concentration increased.

In one aspect, a transition may be observed as the concentration of the radical solution was increased from 10 mg-mL$^{-1}$ to 150 mg-mL$^{-1}$. EPR spectra displayed three singlet peaks at 10 mg-mL$^{-1}$, and with the increase of radical concentration, the singlet peak in between started to merge with the left and right singlet peaks at 30 mg mL$^{-1}$, and formed into a symmetric singlet at 150 mg-mL$^{-1}$. At high 4-Amino-TEMPO concentrations, the number of spins per unit volume is increased and spins are localized in PEGDMA gels. Moreover, the observed spectra are broadened, which is a pattern that may be indicative of high local concentrations of the spin probe (i.e., 4-Amino-TEMPO). In different environments (e.g., engineered hydrogels with different polymer types and molecular weights) or for different radical concentrations, alignment characteristics of spin probes may differ due to localization of spin probes. For instance, spin-labeled cyclodextrin was incorporated into the cross-link points of hydrogel building block comprising polyethylene glycol (PEG) and cyclodextrin (b-CD). EPR spectra of the spin labeled hydrogel building blocks were investigated as a function of the ratio of PEG to b-CD, the length of the PEG chain, the nature of solvent entrapped in the gel structure, and temperature. Here, for 20% PEGDMA, 50% PEGDMA and 5% GelMA hydrogel building blocks, it was shown that regardless of pattern change of singlets, the area under the EPR spectra increased indicating an increased amount of trapped radical and an increased magnetic responsiveness of hydrogels.

Figure 2G:
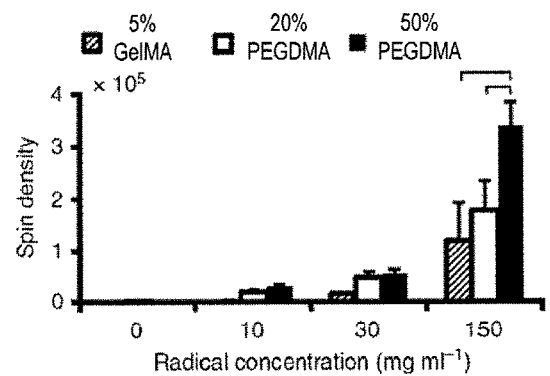
FIG. 2G is a bar graph showing a comparison of spin density as a function of radical concentration for 20% PEGDMA, 50% PEGDMA, and 5% GelMA building blocks after overnight soaking in a stable radical solution including 0, 10, 30, or 150 mg ml$^{-1}$ 4-amino-TEMPO stable radical in PBS. Error bars represent standard deviation from the mean.
Figure 2H:
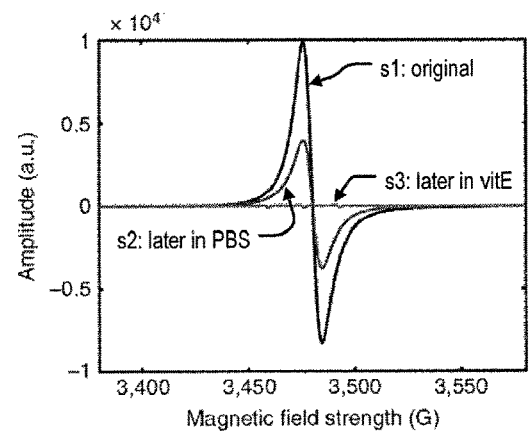
FIG. 2H is an EPR spectra showing amplitude as a function of magnetic field strength for building block samples s1, s2, and s3. Sample s1 was PEGDMA hydrogel building blocks soaked in a stable radical solution. Sample s2 was PEGDMA hydrogel building blocks soaked in a stable radical solution and then transferred into PBS (without vitamin E). Sample s3 was PEGDMA hydrogel building blocks soaked in a stable radical solution and then transferred into solution including 0.5 mg ml$^{-1}$ vitamin E.
Figure 2I:
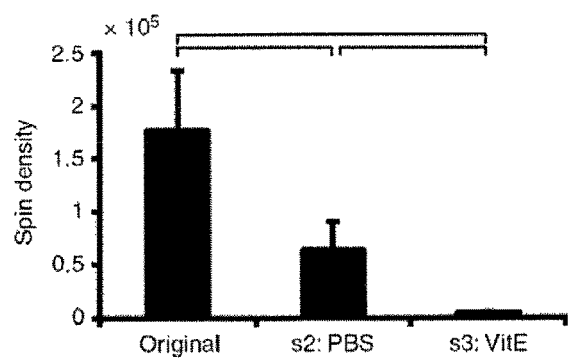
FIG. 2I is a bar graph showing spin densities for samples s1, s2, and s3. Spin densities were calculated computationally by integrating the EPR spectrum of FIG. 2H using the trapezoidal rule. Horizontal lines connecting individual groups represent statistically significant difference ($p<0.05$). Error bars represent standard deviation from the mean.

With reference to FIG. 2G, a comparison of spin density after overnight soaking in a solution comprising stable radicals revealed that 50% PEGDMA exhibited the highest spin density. To switch off the paramagnetism, hydrogel building blocks were treated with an antioxidant solution including vitamin E. As shown in FIG. 2H, spin density of samples treated with the antioxidant solution significantly decreased as compared with the original sample (FIG. 2I), indicating that the amount of free radicals are significantly decreased or neutralized via exposure to the antioxidant vitamin E.

Figure 3F:
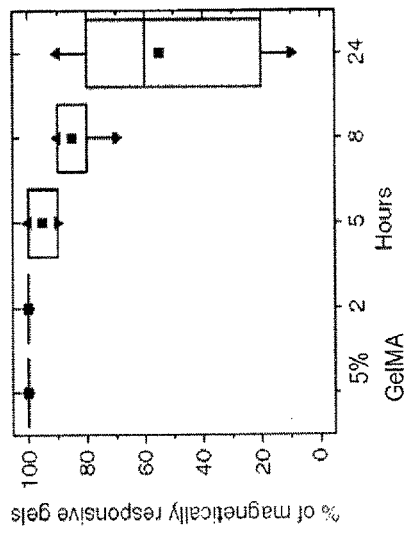
FIG. 3F is a plot of the fraction (%) of hydrogel building blocks that were magnetically responsive following initial exposure to a magnetic field as a function of time for 5% GelMA hydrogel building blocks soaked in a solution including 4-amino-TEMPO stable radical in PBS for 30 min.
Figure 3E:
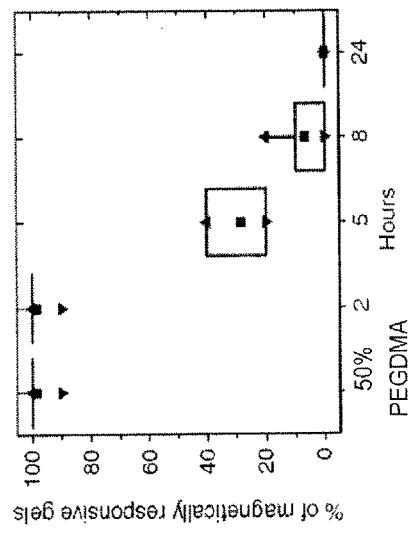
FIG. 3E is a plot of the fraction (%) of hydrogel building blocks that were magnetically responsive following initial exposure to a magnetic field as a function of time for 50% PEGDMA hydrogel building blocks soaked in a solution including 4-amino-TEMPO stable radical in PBS for 30 min.
Figure 3D:
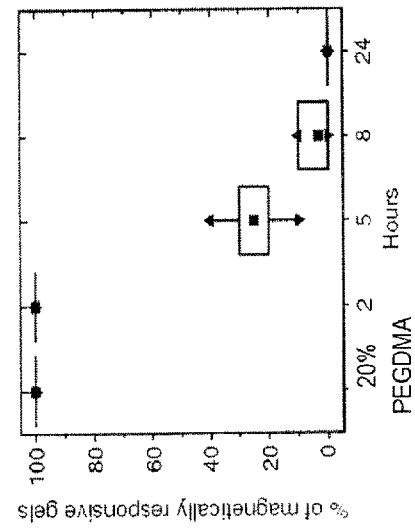
FIG. 3D is a plot of the fraction (%) of hydrogel building blocks that were magnetically responsive following initial exposure to a magnetic field as a function of time for 20% PEGDMA hydrogel building blocks soaked in a solution including 4-amino-TEMPO stable radical in PBS for 30 min.
Figure 3I:
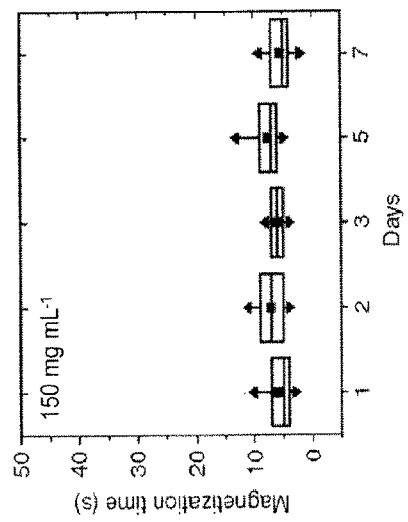
FIG. 3I is a plot of magnetization time as a function of elapsed time following soaking of 20% PEGDMA hydrogel building blocks in a solution including 150 mg ml$^{-1}$ 4-amino-TEMPO stable radical for 1 day.
Figure 3H:
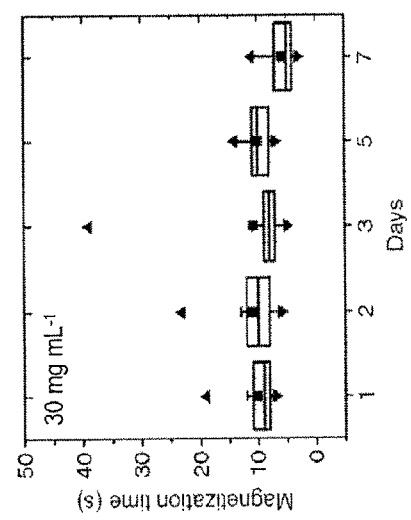
FIG. 3H is a plot of magnetization time as a function of elapsed time following soaking of 20% PEGDMA hydrogel building blocks in a solution including 30 mg ml$^{-1}$ 4-amino-TEMPO stable radical for 1 day.
Figure 3G:
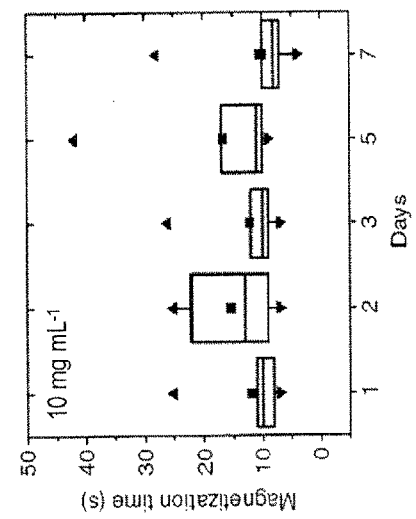
FIG. 3G is a plot of magnetization time as a function of elapsed time following soaking of 20% PEGDMA hydrogel building blocks in a solution including 10 mg ml$^{-1}$ 4-amino-TEMPO stable radical for 1 day.
Figure 3J:
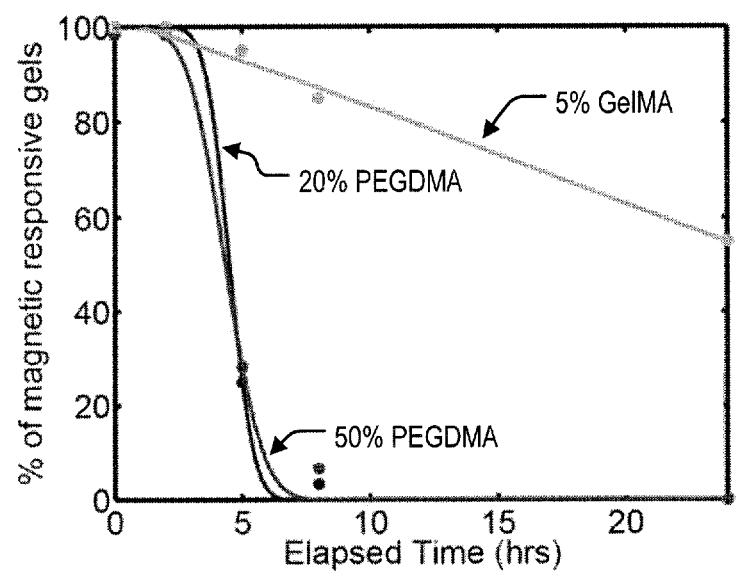
FIG. 3J is a plot of the percent of magnetic responsive gels as a function of elapsed time showing exponential curves fit to data from FIGS. 3D, 3E, and 3F.

To show the versatility of the approach for building blocks prepared with different polymers, magnetic responsiveness of radicalized building units composed of PEGDMA and GelMA were evaluated. In one aspect, it may be useful to incubate or soak hydrogels in solutions comprising stable radicals across a range of concentrations. With reference to FIGS. 3A-3I, hydrogel building blocks were incubated in a solution of 10, 30, or 150 mg ml$^{-1}$ of 4-Amino-TEMPO. Following fabrication and incubation, radicalized hydrogel building blocks were placed in close proximity to an NdFeB permanent magnet. With reference to FIG. 3A, measurements of magnetization time (i.e., the elapsed time until hydrogel building blocks were observed to move in response to the magnetic field) were made. Magnetically responsive hydrogels were counted after exposure to the magnetic field for a period of 15 seconds and 1 minute (FIGS. 3B and 3C). The results showed that more than 90% of building blocks became magnetically responsive within 1 minute. Further, the longevity of the magnetic response of hydrogel building blocks was determined. The percentage of magnetically responsive hydrogel building blocks was calculated for a range of incubation times including 0, 2, 5, 8 and 24 hours (FIGS. 3D-3F). Results show that 5% GelMA building blocks remain magnetically responsive for a longer time period of time as compared with either 20% or 50% PEGDMA building blocks (FIG. 3J). With reference to FIGS. 3G-3I, soaking times of hydrogel building blocks in stable radical solutions were increased to one or more days. Magnetization times and the corresponding deviations decreased as the concentration of the stable radical solution increased, indicating that building blocks may become more responsive to the magnetic field by increasing the soaking time, the concentration of the radical solution, or a combination thereof.

Figure 4A:
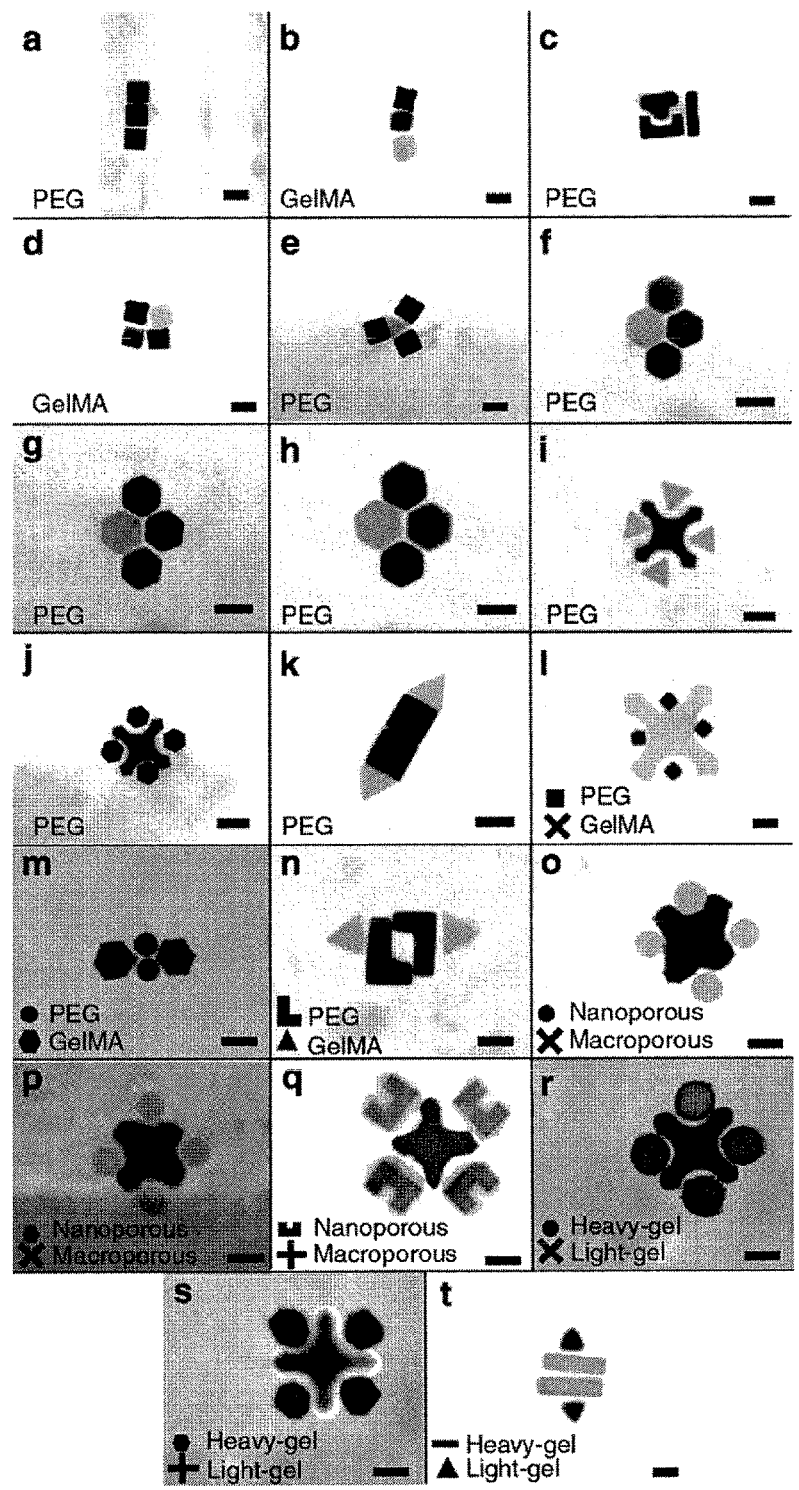
FIG. 4A is a series of images of constructs assembled from building blocks according to the present disclosure. Panels a and b are rod assemblies composed of PEGDMA and GelMA hydrogels. Panel c is a Tetris-like assembly of PEGDMA. Panel d is a Square assembly of GelMA. Panel e is a flower-like assembly of PEGDMA. Panels f-h are hexagonal assemblies of PEGDMA hydrogels. Panels i-k are more complex assemblies of PEGDMA hydrogels. Panels l-n are heterogeneous assemblies including both PEGDMA and GelMA. Panels o-q are heterogeneous porous assemblies including sucrose leached macroporous and nanoporous PEGDMA gels. Panels r-t are assemblies with heterogeneity in mass density (glass bubble encapsulating light PEGDMA gels and heavier PEGDMA gels together).
Figure 4B:
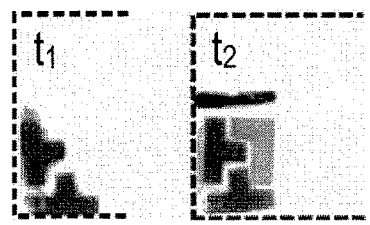
FIG. 4B is a series of images showing self-assembly of a construct at three sequential time points $t_1$, $t_2$, and $t_3$. The scale bar represents 1 mm.
Figure 4B:
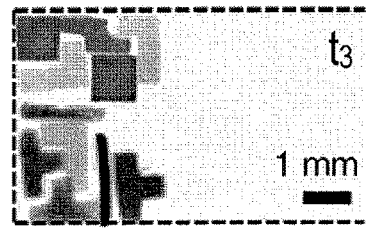
Figure 4C:
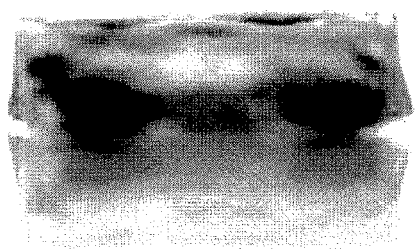
FIG. 4C is a side elevational view of a 3D heterogeneous gel composed of three layers of macroporous (x-shape) and nanoporous (o-shape) 50% PEGDMA gels.
Figure 4D:
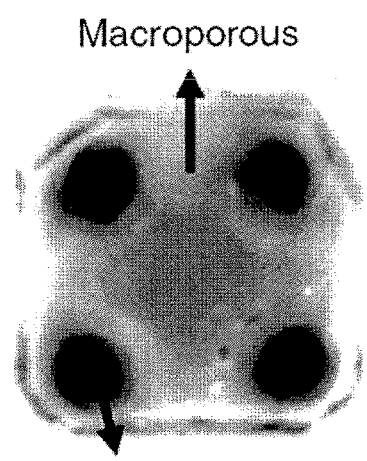
FIG. 4D is a top plan view of the gel of FIG. 4C. Gel cross-section is 5 mm×5 mm.

Following characterization and quantification of paramagnetism, hydrogels are self-assembled with the guidance of a magnetic field into heterogeneous patterns at the interface of a liquid medium with the air. Turning now to FIG. 4A, various constructs may be prepared from building blocks composed of PEGDMA and GelMA hydrogel. In one aspect, a change in polymer concentration of the building blocks may change the contact angle between the suspending liquid medium and the individual building blocks, and thus the meniscus forming between building blocks in the assembled construct configuration. This, in turn, may affect the gradients of liquid surface curvature and capillary forces (FIG. 4G). In one aspect, building blocks may be programmed by composition to provide heterogeneous constructs composed of building blocks fabricated from different polymers (panels i-n of FIG. 4A) In another aspect, macroporous hydrogel building blocks may be prepared by sucrose leaching (Park, et al., *Biotechnol. Bioeng.* 106, 138-148, (2010)) and assembled with nanoporous hydrogels into complex shapes (panels o-q). In yet another aspect, glass bubbles (density=0.46 g cm$^{-3}$) may be encapsulated in building blocks to fabricate gels with lower mass density than normal glass-bubble-free building blocks. Heterogeneous assemblies with varying mass densities (glass bubble encapsulating light PEGDMA gels and heavier PEGDMA gels together) may also be prepared as shown in panels r-t.

To demonstrate the dynamic orientation control capability of the present disclosure for manipulating and guiding assembly of a variety of micro-scale building blocks, n construct assembled from tetromino building blocks was prepared using a reservoir similar that the reservoir 126 in FIG. 1C. Building blocks of various shapes including zig-zag, rod, square and T-polyomino were distributed at various starting locations or wells within a reservoir as shown in FIG. 4H and assembly was monitored over time as shown in FIG. 4B.

Ultimate shape control may depend on the amount of stable radicals included in the soaking solution. Theoretically, excessive amounts of stable radicals may amplify the magnetic susceptibility of the building blocks thereby providing a greater response in the presence of a magnetic field regardless of distances between each building block and permanent magnet. This may lead to decreased control over motion of individual building blocks (numerous blocks move simultaneously towards high magnetic field strength). This approach may be useful for (unguided) self-assembly. On the other hand, limited use of stable radicals may enable control of individual building block. Further, it may be useful to reduce the concentration of free radicals in order to reduce any potential negative effects the free radicals may have on cells or other biological materials prior to treatment with an antioxidant. In another aspect, to stabilize the ultimate overall shape of the assembled construct, it may be useful to drain the reservoir liquid and then perform a secondary cross-linking to attach each of the building blocks to one another with a construct.

3D soft materials with multiple complex failure modes may have several applications in tissue engineering such as to investigate dynamic response of soft tissue surrogates during impact, or in soft robotics to create actuating or transmission components with different Young's moduli. In some embodiments, the present disclosure may enable fabrication of 3D structures. For example, building blocks may be first assembled into 2D constructs. Next, the liquid medium may be drained or otherwise recovered from the reservoir while leaving the construct behind. Then, a secondary cross-linking step may be carried out to stabilize the construct. Further, vitamin E or another antioxidant may be used to treat the construct to neutralize, at least in part, the stable radicals present in the construct. In a next step, embryo-tested mineral oil and fresh liquid medium may be sequentially added to the reservoir containing the construct. This step may enable the construct to remain submerged in the first liquid phase (i.e., the mineral oil) at the bottom of reservoir with the fresh liquid medium forming a second liquid phase on top of the first liquid phase. Next, self-assembly of another set of building blocks into a second construct may be carried out at or about the location where the first (previous) construct was assembled. That is, the second construct may be assembled in the second liquid phase relatively above the first construct. Thereafter, both liquid phases may be drained out of the reservoir to layer the second construct on top of the first construct. This process may be repeated one or more times to provide a three or more layered structure as in FIGS. 4C and 4D.

Figure 4E:
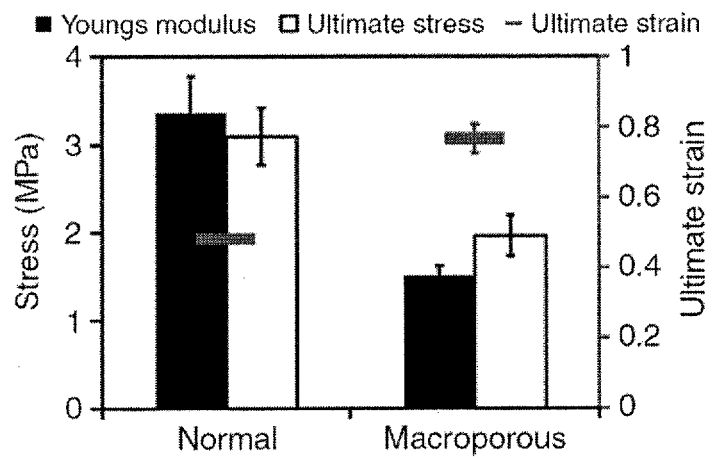
FIG. 4E is a bar graph showing Young's Modulus, Ultimate Stress, and Ultimate Strain for normal and macroporous gels. Error bars represent standard error of the mean.
Figure 4F:
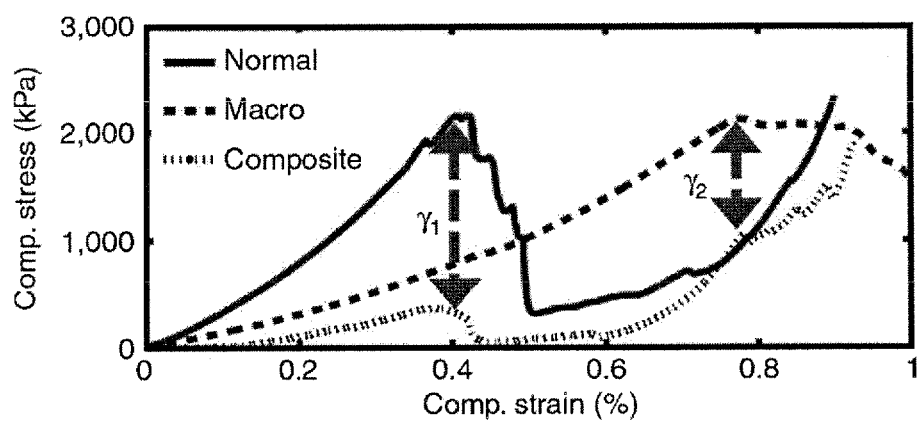
FIG. 4F is a plot of compressive stress as a function of compressive strain for normal (solid), macroporous (dashed) and composite (dotted) hydrogel building blocks.
Figure 4G:
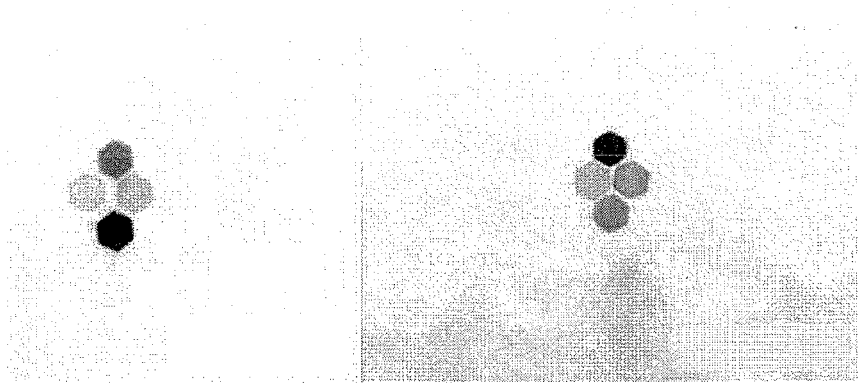
FIG. 4G is an image of paramagnetic assembly of PEGDMA 20% (left) and PEGDMA 50% gels (right).
Figure 4H:
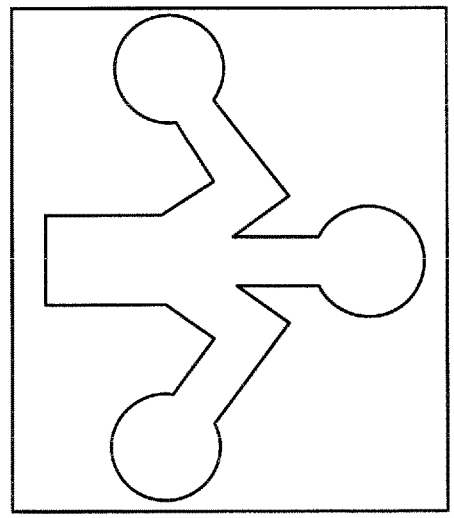
FIG. 4H is a schematic illustration of another embodiment of a reservoir for self assembly of building blocks. Circular wells provide starting locations for different groups of building blocks.

In one aspect, mechanical compression tests may be performed to determine Young's Modulus of 20% PEGDMA gels (normal), sucrose-leached macroporous 20% PEGDMA gels and composite gels (FIG. 4E). Compressive stress versus compressive strain curves (FIG. 4F) show that the composite building blocks may show two distinct failures, which particularly match with the ultimate strain of normal and macroporous gels. In addition ultimate stress (τ) ratios at failure strains, that is $$\gamma_1 = \frac{\tau_{normal}}{\tau_{composite}}; \gamma_2 = \frac{\tau_{macroporous}}{\tau_{composite}}$$

are at the order of cross-section area ratios of normal and macroporous gels in the composite building blocks as shown in FIG. 4F, which indicates that four columns (normal cylindrical gels) may initially fail within the composite gel, and then remaining macroporous structure holds the integrity of composite gel until the secondary failure.

Figure 5A:
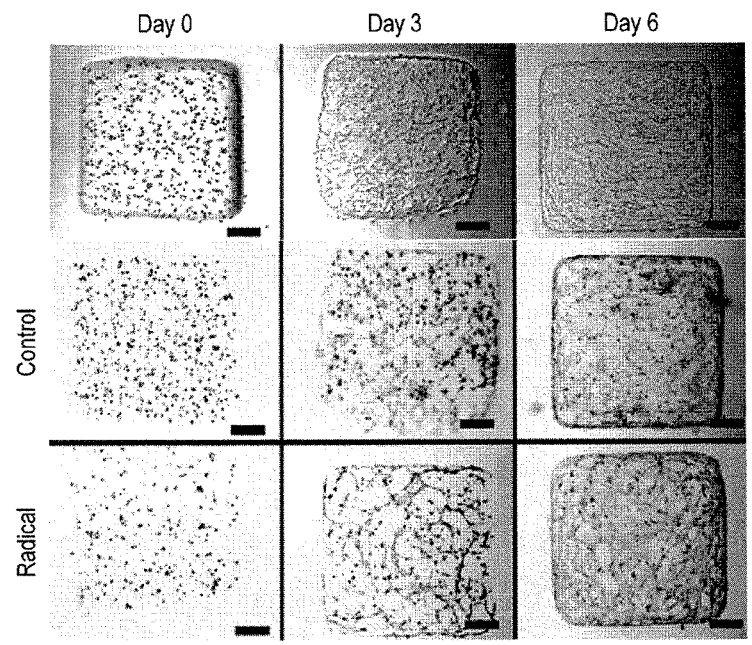
FIG. 5A is a series of images including bright-field (control) and fluorescence images of 3T3 cells encapsulated in GelMA hydrogels shown at 0, 3, and 6 days (top to bottom) for a control group (no stable radicals) and for a radical group soaked in 30 mg ml$^{-1}$ 4-amino-TEMPO for 30 min.
Figure 5B:
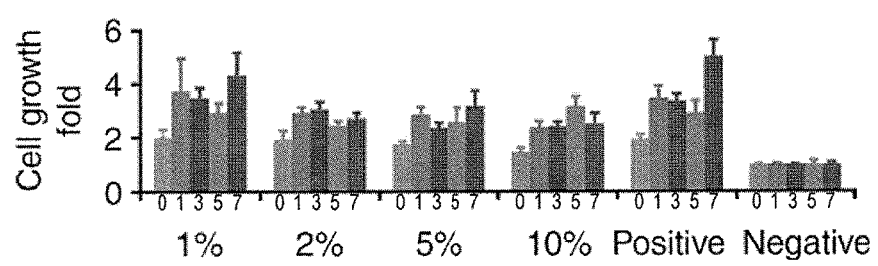
FIG. 5B is a bar graph showing MTT (3-[4,5-dimethyl-thiazol-2-yl]-2,5 diphenyl tetrazolium bromide) assay results as a function of volume-to-volume ratios (v/v) of added stable radical suspension volume to cell suspension volume at 0, 1, 3, 5 and 7 days. The histograms showed proliferation of cells in the presence of stable radicals. Positive control represents cells without radicals. Negative control is only the MTT reagents. All results were normalized with respect to negative control. Error bars represent standard error of the mean. From left to right for each grouping of bars: 0 days, 1 days, 3 days, 5 days, and 7 days.

The organization and coding of cell-encapsulating hydrogels may have broad applications in several fields including regenerative medicine, cell-based pharmaceutical research and tissue engineering. Embodiments of the present disclosure may provide a high level of control over complex tissue microenvironments. To this end, the effects of stable radicals on cell viability and proliferation were evaluated. With reference to FIG. 5A, bright-field and fluorescence images of 3T3 cells encapsulated in GelMA hydrogels were imaged at 0, 3, and 6 days for a control group (no stable radicals) and for a stable radical group soaked in a solution of 30 mg ml$^{-1}$ 4-amino-TEMPO for 30 min. Results showed that 3T3 cells proliferated within all hydrogel groups including the stable radical containing group (FIG. 5J). Further, MTT (3-(4,5-dimethylthiazol-2-yl)-2,5-diphenyl tetrazolium bromide) analysis was performed to investigate proliferation of cells in the presence of radicals and vitamin E (FIG. 5B-5F). Cell growth was plotted as a function of volume-to-volume ratios (v/v) of added radical suspension volume to cell suspension volume for days 0, 1, 3, 5 and 7, which showed proliferation of cells in the presence of stable radicals (FIGS. 5B and 5K).

Figure 5C:
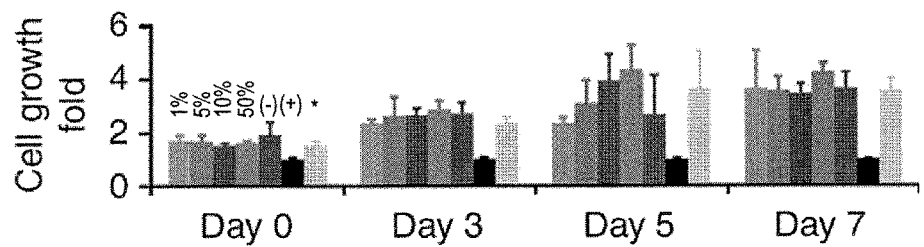
FIG. 5C is a bar graph showing cell growth after 0, 3, 5, and 7 days. Hydrogel building blocks were soaked in a stable radical solution including 30 mg ml$^{-1}$ 4-amino-TEMPO for 30 min, and then exposed to antioxidant solutions including 1, 5, 10, or 50% vitamin E. Error bars represent standard error of the mean. From left to right for each grouping of bars: 1% vitamin E, 5% vitamin E, 10% vitamin E, 50% vitamin E, negative control, positive control, and radical control.
Figure 5D:
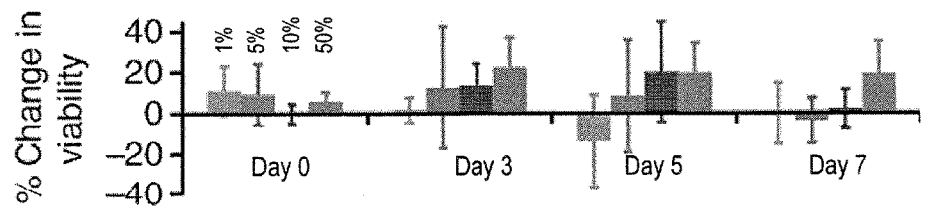
FIG. 5D is a bar graph showing % change in cell viability corresponding to FIG. 5C. From left to right for each grouping of bars: 1% vitamin E, 5% vitamin E, 10% vitamin E, and 50% vitamin E.
Figure 5E:
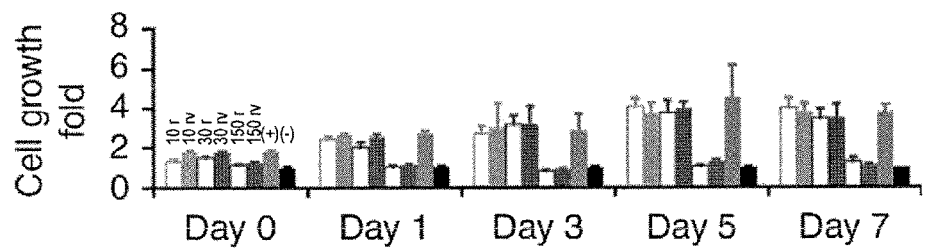
FIG. 5E is a bar graph showing cell growth after 0, 1, 3, 5, and 7 days. Hydrogel building blocks were soaked in stable radical solutions including 10, 30, or 150 mg ml$^{-1}$ 4-amino-TEMPO and exposed to vitamin E solution (100% (v/v)). Labels with 'r' in the figure caption, such as '10 r', corresponds to hydrogels soaked in a stable radical solution including 10 mg ml$^{-1}$, and labels with 'rv' corresponds to gels exposed to vitamin E following soaking. Results showed that for large concentration of radical, for example, 150 mg ml$^{-1}$ (and for 30 min incubation), vitamin E does not significantly help to recover cells. Error bars represent standard error of the mean. From left to right for each grouping of bars: 10 r, 10 rv, 30 r, 30 rv, 150 r, 150 rv, positive control, negative control.
Figure 5F:
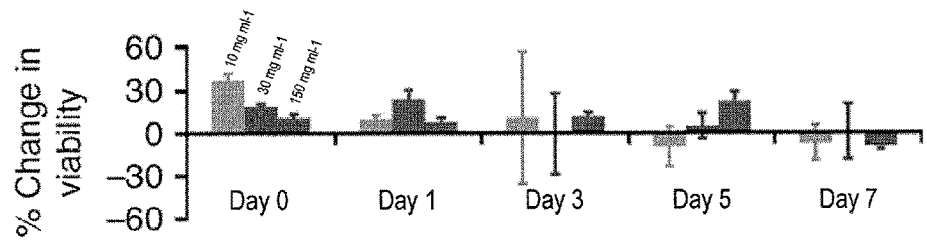
FIG. 5F is a bar graph showing % change in cell viability corresponding to FIG. 5E. From left to right for each grouping of bars: 10 mg ml$^{-1}$, 30 mg ml$^{-1}$, and 150 mg ml$^{-1}$ 4-amino-TEMPO.

After paramagnetizing (soaking) hydrogel building blocks with stable radicals (30 mg ml$^{-1}$ 4-amino-TEMPO for 30 min), exposing the building blocks to a vitamin E solution for a range of vitamin E solution volume to cell suspension volume ratios, resulted in an increase of cell proliferation for greater than 50% (v/v) vitamin E solution (FIGS. 5C and 5D). In another aspect, the effects of stable radicals on cell viability and proliferation were measured by evaluating cell viability for a range of stable radical concentrations including 10, 30 and 150 mg ml$^{-1}$ 4-amino-TEMPO, while keeping vitamin E solution constant at 100% (v/v). Results showed that for large concentrations of stable radicals, vitamin E may not significantly help to recover cells.

Figure 5G:
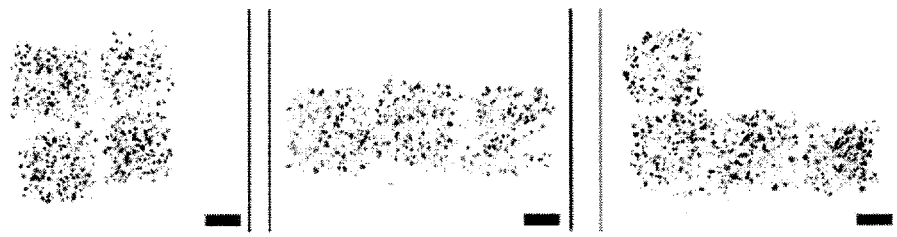
FIG. 5G is a series of fluorescent image of square (left), rod-shaped (middle), and L-shaped (right) constructs of 3T3 encapsulating GelMA hydrogel building blocks. Scale bars are 200 µm. Images are inverted for clarity.
Figure 5H:
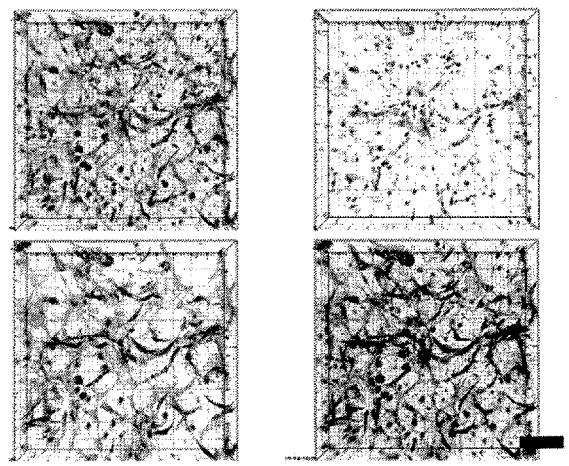
FIG. 5H is a series of fluorescent images of cardiomyocyte encapsulating GelMA hydrogel building blocks for a control sample including no stable radicals. Cells were stained with mouse anti-α-actinin (sarcomeric) and anti-GATA-4. Actin cytoskeleton was visualized with phalloidin and DAPI was used as nuclear counter staining. All images were shown on day 10. The scale bar represents 200 µm. Images are inverted for clarity.
Figure 5I:
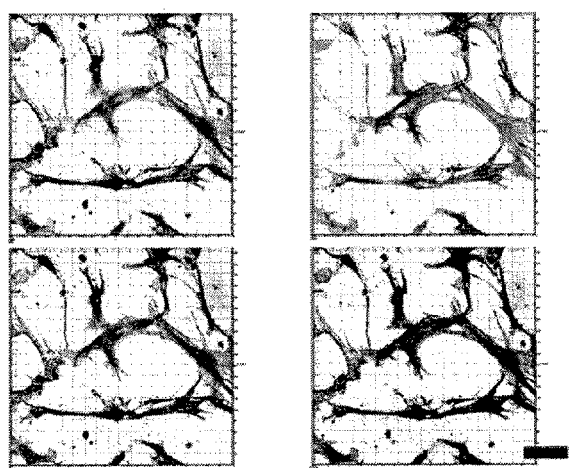
FIG. 5I is a series of fluorescent images of cardiomyocyte encapsulating GelMA hydrogel building blocks for a sample at 40× magnification of stable radical and vitamin E exposed gels. Cells were stained with mouse anti-α-actinin (sarcomeric) and anti-GATA-4. Actin cytoskeleton was visualized with phalloidin and DAPI was used as nuclear counter staining. All images were shown on day 10. The scale bar represents 100 µm. Images are inverted for clarity.
Figure 5J:
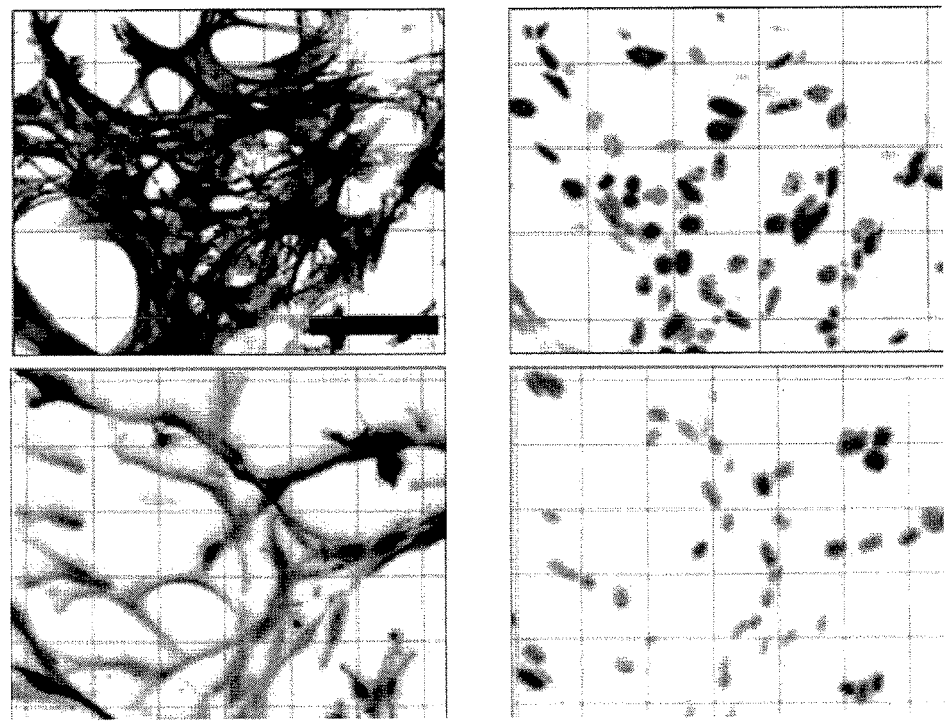
FIG. 5J is a series of fluorescence image showing immunocytochemistry staining of 3T3 encapsulating GelMA hydrogel building blocks. Hydrogels were soaked in stable radical solutions including either 10 mg ml$^{-1}$ 4-amino-TEMPO (top left, top right) or 30 mg ml$^{-1}$ 4-amino-TEMPO (bottom left, bottom right), and then a solution including vitamin E. Cells in GelMA hydrogels were stained with Ki67 nuclear proliferation specific marker. Phalloidin Alexa Flour 647 and DAPI show cytoskeleton and nuclei of cells, respectively. Images at the top left and bottom left are with phalloidin and Ki67, and images at the top right and bottom right are with DAPI and Ki67. Scale bar is 100 µm.
Figure 5K:
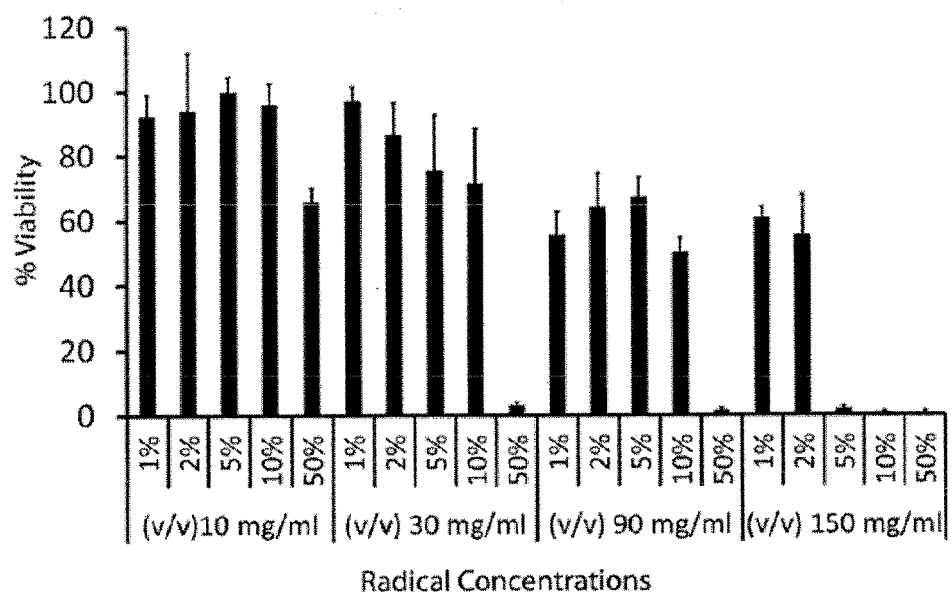
FIG. 5K is a bar graph showing the viability of 3T3 cells incubated with different concentration of stable radical solutions including 10, 30, 90, and 150 mg ml$^{-1}$ 4-amino-TEMPO and for a range of volume-to-volume ratio of radical solution to cell suspension volume including 1, 2, 5, 10, and 50%. MTT assay was performed to analyze the viability of 3T3 cells immediately after incubation with different concentrations of stable radicals.

Faster actuation of radical-impregnated hydrogel building blocks may require higher concentrations of radicals, which in turn may be more difficult to quench or neutralize with vitamin E. Cell growth and functionality may be reduced significantly when high concentrations of radicals (150 mg ml$^{-1}$ 4-amino-TEMPO) are utilized for magnetization of hydrogels. In one aspect, the viability of 3T3 cells after assembly into square, rod-shaped and L-shaped constructs is shown in FIG. 5G. Further, primary cardiomyocytes were isolated and encapsulated into GelMA hydrogel building blocks as shown in FIGS. 5H and 5I). Results show that cardiomyocytes may preserve their phenotypic properties and functionalities after radical exposure and vitamin E recovery at day 10.

Figure 6A:
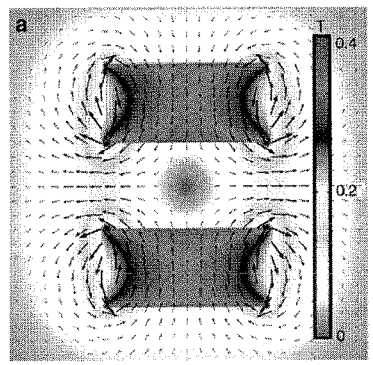

In another embodiment, the present disclosure may provide a system and method for the levitational and guided self-assembly of building blocks using stable radicals. Aqueous solutions of gadolinium (Gd$^{3+}$) and manganese (Mn$^{+2}$) ion salts can be used for levitation of beads and particles. In one aspect, the use of radicals in levitational guided self-assembly of soft and rigid objects was explored. A magnetic setup including two permanent NdFeB magnets in anti-Helmholtz configuration (like poles facing each other) was fabricated to levitate building blocks. The simulation of magnetic field norm (contour) and flux density (arrows) created by the magnetic setup (FIG. 6A) shows that magnetic field may reach a minimum at the centre of symmetry axes (FIGS. 6K and 6L).

For a relatively diamagnetic hydrogel building block suspended in a paramagnetic solution under an applied magnetic field, B, equation (1) gives the magnetic force, $F_m$, and equation (2) gives the force of gravity, $F_g$, acting on the hydrogel building block.

$$F_m = \left(\frac{\chi_{gel} - \chi_m}{\mu_0}\right) V(B \cdot \nabla) B \quad \text{(Eq. 1)}$$

$$F_g = (\rho_{gel} - \rho_m) V g \quad \text{(Eq. 2)}$$

In these equations, $\chi_m$ is the non-dimensional magnetic susceptibility of the paramagnetic medium and $\chi_{gel}$ is the non-dimensional magnetic susceptibility of the suspended hydrogel building block, $\mu_0 = 4\pi \times 10^{-7} = 4$ (N·A$^{-2}$) is the magnetic permeability of free space, V (m$^3$) is the volume of the hydrogel building block, $\rho_{gel}$ (kg·m$^{-3}$) is the density of the hydrogel building block, $\rho_m$ (kg·m$^{-3}$) is the density of the paramagnetic liquid medium, and g is the vector of gravity. It is assumed that hydrogel building block has a homogeneous density distribution and magnetic susceptibility throughout its volume. The gravitational force (corrected for the effect of buoyancy), $F_g$, is always directed to or away from the center of the Earth, and the magnitude of this force does not depend on the position of the hydrogel building block inside the reservoir as long as the densities of the paramagnetic medium and the hydrogel building block remain constant for the duration of the levitation experiment. The magnetic force acting on the relatively diamagnetic hydrogel building block, $F_m$, is directed towards the minimum of the magnetic field, B, and the magnitude of this force depends on the position of hydrogel building block in the magnetic field. In a transient case (i.e., before hydrogel building block reaches equilibrium point where magnetic forces balance with the gravity force), inertial forces, (i.e., the term at the left in equation (3)), and drag force, $F_d$, which is correlated with the migration velocity of the hydrogel building block, equation 5, will be active as described in equation 3. At equilibrium, the drag and inertial forces vanish, and the magnetic and gravitational forces acting on the hydrogel building block will balance each other (equation 4).

$$ma = F_m + F_g + F_d \quad (Eq. 3)$$

$$F_g + F_m = (\rho_{gel} - \rho_m)Vg + \left(\frac{\chi_{gel} - \chi_m}{\mu_0}\right)V(B\cdot\nabla)B = 0 \quad (Eq. 4)$$

$$F_d = 6\pi\eta R v \quad (Eq. 5)$$

$$F_g = (\rho_{gel} - \rho_m)Vg = \begin{pmatrix} 0 \\ 0 \\ -(\rho_{gel} - \rho_m) \end{pmatrix} \quad (Eq. 6)$$

$$F_m = \left(\frac{\chi_{gel} - \chi_m}{\mu_0}\right)V(B\cdot\nabla)B = \quad (Eq. 7)$$

$$\begin{pmatrix} \left(\frac{\chi_{gel}-\chi_m}{\mu_0}\right)V\left(B_x\frac{\partial B_x}{\partial x}+B_y\frac{\partial B_x}{\partial y}+B_z\frac{\partial B_x}{\partial z}\right) \\ \left(\frac{\chi_{gel}-\chi_m}{\mu_0}\right)V\left(B_x\frac{\partial B_y}{\partial x}+B_y\frac{\partial B_y}{\partial y}+B_z\frac{\partial B_y}{\partial z}\right) \\ \left(\frac{\chi_{gel}-\chi_m}{\mu_0}\right)V\left(B_x\frac{\partial B_z}{\partial x}+B_y\frac{\partial B_z}{\partial y}+B_z\frac{\partial B_z}{\partial z}\right) \end{pmatrix}$$

The exact analytical expression describing the magnetic field between two identical rectangular permanent magnets in an anti-Helmholtz configuration in 3D is fairly complex. In a 3D Cartesian coordinate system in which the z-axis is aligned with the direction of the vector of gravity, g=(0, 0, −g), the balance of forces simplifies to yield equation 8, because these forces balance each other only along the z-axis, $$(\rho_{gel}-\rho_m)Vg + \left(\frac{\chi_{gel}-\chi_m}{\mu_0}\right)V\left(B_x\frac{\partial B_z}{\partial x}+B_y\frac{\partial B_z}{\partial y}+B_z\frac{\partial B_z}{\partial z}\right)=0 \quad (Eq. 8)$$

Along the centerline, the absolute value of the third term $$\left(B_z\frac{\partial B_z}{\partial z}\right)$$

in equation 8 is at least 10$^3$ times larger than the absolute value of the sum of the first and second terms $$\left(B_x\frac{\partial B_z}{\partial x}+B_y\frac{\partial B_z}{\partial y}\right): \quad (Eq. 9)$$

$$B_z\frac{\partial B_z}{\partial z} \gg \left(B_x\frac{\partial B_z}{\partial x}+B_y\frac{\partial B_z}{\partial y}\right)$$

With the magnets used in some embodiments (NdFeB, 5 cm×5 cm×2.5 cm), $B_z$ varies virtually linearly with z (the distance from the surface of the bottom magnet), from a maximum of +$B_0$ at the surface of the bottom magnet (z=0) to a minimum of −$B_0$ at the surface of the top magnet (z=d), if the separation between the magnets, d, is less than or equal to approximately 45 mm. Because of this linearity, the magnetic field along the centerline may be approximated with equation 10.

$$B = \begin{pmatrix} B_x \\ B_y \\ B_z \end{pmatrix} = \begin{pmatrix} 0 \\ 0 \\ -\frac{2B_0}{d}z + B_0 \end{pmatrix} \quad (Eq. 10)$$

Equation 8 is solved using the explicit expression for the magnetic field (equation 10) to find the equilibrium point, $z_{eq}$ (m), between the two magnets where the force of gravity and the magnetic force acting on the hydrogel unit balance each other (equation 11).

$$z_{eq} = \frac{(\rho_{object}-\rho_m)g\mu_0 d^2}{(\chi_{gel}-\chi_m)4B_0^2} + \frac{d}{2} \quad (Eq. 11)$$

Equilibrium height as a function of distance between object and surrounding medium is plotted in FIG. 6L.

Figure 6B:
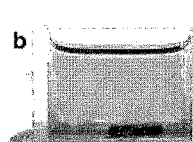
FIG. 6B is an image of a 1×1 cm$^2$ 20% PEGDMA hydrogel in a radical solution reservoir before being placed into a magnetic setup composed of permanent NdFeB magnets in anti-Helmholtz configuration (same poles facing each other).
Figure 6C:
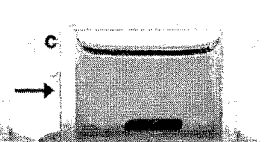
FIG. 6C is an image of the hydrogel of FIG. 6B after being placed into a magnetic setup composed of permanent NdFeB magnets in anti-Helmholtz configuration (same poles facing each other).
Figure 6D:
FIG. 6D is an image of a non-radicalized (left) and radicalized (right) 1×1 cm$^2$ hydrogels in Gadolinium (Gd) solution before being placed into a magnetic setup as in FIG. 6C.
Figure 6E:
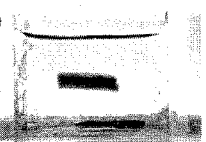
FIG. 6E is an image of the hydrogels of FIG. 6D after being placed into a magnetic setup as in FIG. 6C.

In one example, a 1 cm×1 cm×1.5 mm 20% PEGDMA hydrogel was suspended in a radical solution as shown in FIG. 6B) and the reservoir was placed into the magnetic setup as shown in FIG. 6C), which results in levitation of hydrogel building block because of the paramagnetism of radical solution. To illustrate the competing effects in the presence of both radicals and conventionally used ion salts, two samples were prepared including a non-radicalized hydrogel building block (gel at left, FIG. 6D) and radicalized hydrogel building block (gel at right, FIG. 6D) and placed into a Gadolinium (Gd) solution. The non-radicalized hydrogel building block that does not have a significant magnetic signature levitates because of the paramagnetism of Gd solution. On the other hand, the radicalized hydrogel building block does not levitate due to cancelling effects among paramagnetisms of radicals and Gd ion salts (FIG. 6E).

Figure 6F:
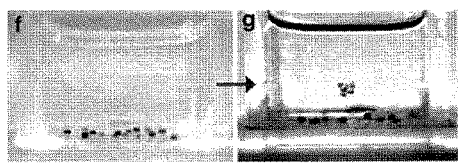
FIG. 6F is an image of a non-radicalized and radicalized 1×1 mm$^2$ hydrogels in Gd solution before being placed into a magnetic setup as in FIG. 6C.
Figure 6G:
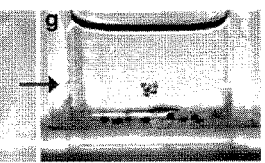
FIG. 6G is an image of the hydrogels of FIG. 6F after being placed into a magnetic setup as in FIG. 6C.
Figure 6I:
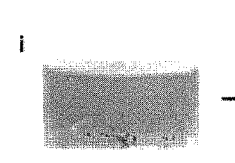
FIG. 6I is an image of the system of FIG. 6H taken before assembly in radical solution.
Figure 6J:
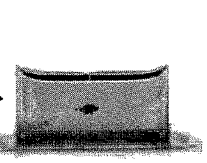
FIG. 6J is an image of the system of FIG. 6H taken after assembly in radical solution.
Figure 6H:
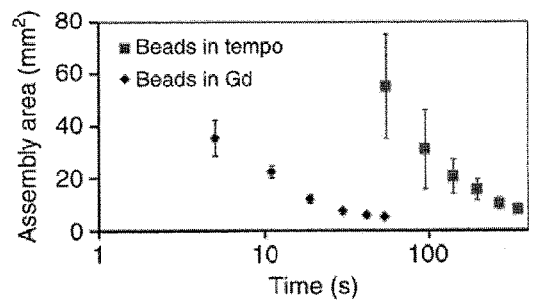
FIG. 6H is plot showing assembly area as a function of time for the levitational guided self-assembly of 500 µm polystyrene beads in Gd and radical solution. Error bars represent standard deviation from the mean.
Figure 6K:
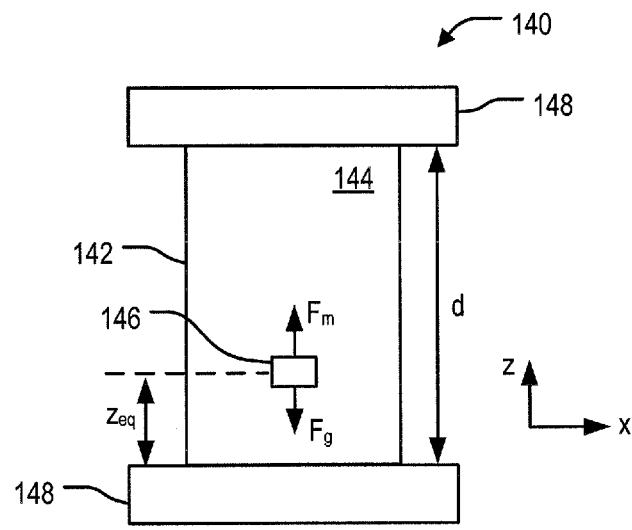
FIG. 6K is a Schematic of an example system for levitation according to the present disclosure.
Figure 6L:
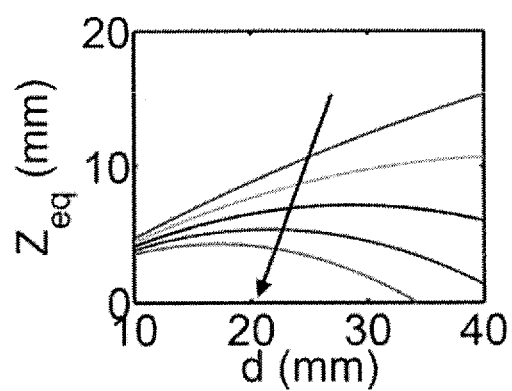
FIG. 6L is a plot of analytical equilibration height as a function of distance between two magnets in anti-Helmholtz configuration for a range of density difference ($\rho_{bead}-\rho_m$) between beads and suspension liquid. In the arrow direction, density difference increases. Suspension liquid is 0.141 M Gd, gap between two magnets=26 mm, magnitude of the magnetic field in the center of the top surface of the bottom magnet=0.375 T.
Figure 6M:
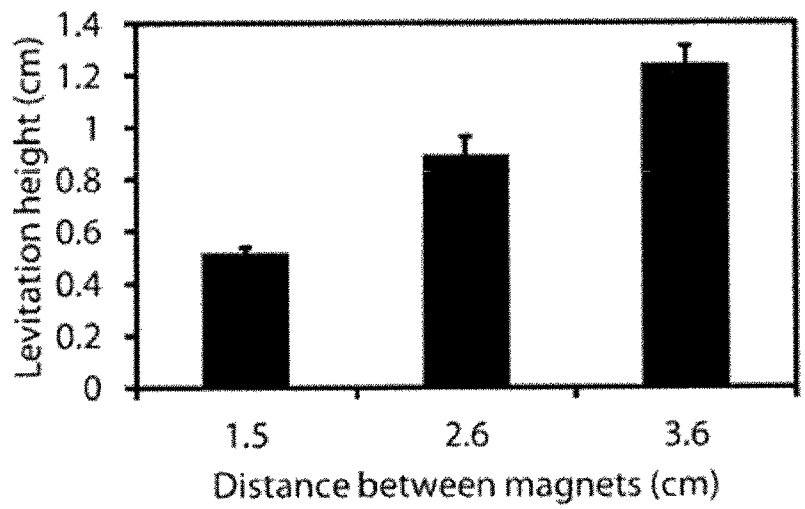
FIG. 6M is a bar chart showing the effect of distance between two magnets in anti-Helmholtz configuration on levitational self-assembly height. Magnets were in contact with bottom and top surfaces of a chamber. Experiments were performed for a range of distances including 1.5 cm, 2.6 cm, and 3.6 cm. Levitation height was calculated by averaging the most top and most bottom point of assembled building blocks.
Figure 6N:
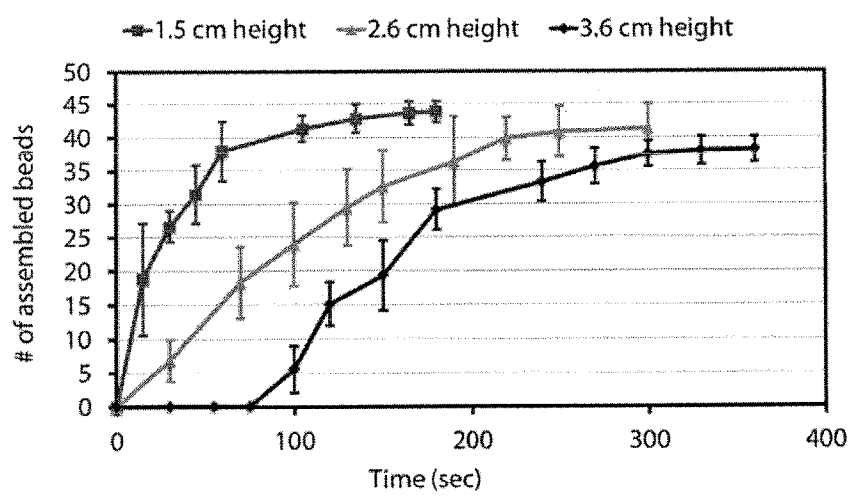
FIG. 6N is a plot showing the number of assembled beads (building blocks) as a function of time. 45 beads were placed into a reservoir in all experiments.

In another aspect, smaller and multiple hydrogel building blocks of each type (radicalized and non-radicalized) were used to demonstrate selective assembly of gels. Radicalized hydrogel building blocks do not levitate because of cancelling effects between paramagnetism of radicals and Gd ion salts, whereas non-radicalized hydrogel building blocks are levitated and assembled because of paramagnetism of Gd solution (FIGS. 6F and 6G). Further, 500 μm polystyrene beads were used to quantify temporal changes of the assembly areas in Gd and radical solutions (FIG. 6H). Snapshots were taken before (FIG. 6I) and after (FIG. 6J) assembly in radical solution. An increase in the distance between two magnets led to an increase in levitation height of beads in radical solution (FIGS. 6M and 6N).

In one aspect, the present disclosure may provide a system and a method to pattern multi-component structures that can differentiate among each other by shape, color, and material properties such as mass density, elastic modulus, and porosity. In one aspect the structure or constructs may be prepared by guiding the self-assembly of various building blocks at an air-fluid interface via paramagnetism or within a radical medium via diamagnetism.

In some embodiments, a permanent magnet-based approach may provide a broadly applicable and versatile self-assembly system and method. In one aspect, external power or electricity may be omitted. In another aspect, creating patterns of magnetic field gradient with permanent magnets and guiding self-assembly of components from their reservoirs may be relatively simple and inexpensive. In yet another aspect, based on initial soaking radical concentration of each component, magnetic susceptibilities and thus responses to magnetic field may be manipulated. Further, size and composition of components may be varied, which effects drag forces exerted on floating components, which in turn effects actuation speed of components. Therefore, a number of components may be manipulated in parallel by permanent magnets. In a further aspect, the presented guided and magnetic self-assembly strategy may enable alignment, positioning, and patterning of materials of varying length-scales into functional three dimensional (3D) structures with heterogeneous density, elastic modulus, and porosity in a contact free manner.

In another aspect, for levitational assembly, density may be regulated (e.g., by changing the polymer percentage of hydrogels), which may be used to equilibrate building blocks at different levitational heights in 3D space. Further, density may be engineered in a spatially heterogeneous manner within building blocks to change their equilibrium orientation in 3D. In yet another aspect, for diamagnetic levitational and paramagnetic actuation, assembly may take place in a fluid and at the interface of liquid and air, respectively, and therefore objects may not need to contact solid surfaces. Furthermore, fluid medium excludes stiction, contact adhesion, dry friction, and static charging. In a further aspect, levitational assembly may be performed inside a completely closed chamber or system.

In some embodiments, constant magnetic field lines are created using a permanent magnet system. Moreover, the permanent magnet system may provide a minimum magnetic field strength location which is spatially constant and dictates the levitation heights of hydrogels or beads. By using alternating current, the magnetic field may be changed in direction and intensity, as well as minimum field strength location. Alternating magnetic field may add new capabilities such as changing levitation height over the time. In one aspect, alternating magnetic fields have been used to heat superparamagnetic particles by Neel relaxation and create localized heated spots. In some embodiments, alternating magnetic fields may provide a similar capability to levitate hydrogels or beads. Additionally (or alternatively), permanent magnets are generally portable and inexpensive to fabricate, and may not require additional external equipment as compared to alternating magnetic field setups.

In some embodiments, magnetization of microcomponents via free radicals may be compatible with various techniques such as staining, cell encapsulation, engineering macroporosity, or the like. In one aspect, these techniques may be performed before radical exposure of gels for magnetization. In another aspect, MNP encapsulating hydrogel building blocks may be fabricated by mixing MNPs with prepolymer solution and cell suspension prior to crosslinking. However, it may be useful to selectively impregnate building blocks with radicals as during subsequent processing steps, cells or other materials may be exposed to the MNPs. In another aspect, stable radical-impregnated hydrogels may allow more stable and robust actuation as compared with hydrogels magnetized via free radicals resulting from UV fabrication. In some embodiments, radicals may be encapsulated into shells or capsules. Further, the shells or capsules may be engineered to regulate the interaction between cells and radicals.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

For the fabrication of microgels building blocks, PEGDMA microgel prepolymer solution was prepared by dissolving poly(ethylene glycol) 1000 dimethacrylate (PEGDMA; Polysciences, Inc.; 20%, 50% (w/v)) in PBS (Gibco; 1 ml). Photoinitiator (PI) 2-hydroxy-1-(4-(hydroxyethoxy)phenyl)-2-methyl-1-propanone (1%, w/v, Irgacure 2959; CIBA Chemicals) was then added to the prepolymer solution. 40 μl PEGDMA prepolymer solution was pipetted between spacers (coverslip 25×25 mm$^2$, thickness: 150 μm) on the backside of 95×15 mm$^2$ Pyrex reusable Petri dish (Fisher Scientific). Another coverslip was placed onto the droplet. A photomask (1×1 mm$^2$; square) was set on the coverslip between the UV light and prepolymer droplet. Microgels were fabricated by applying UV light (6.9 W cm$^{-2}$; at a height of 50 mm above the microgels) for 30 s. Then, photomask and coverslip were removed, and square PEGDMA microgels were formed on the coverslip. By using a razor (American Safety Razor, American Line), the microgels were transferred into PBS filled assembly chambers.

GelMA microgel prepolymer solution was prepared by dissolving gelatin methacrylate lyophilized powder (5% (w/v)) in PBS (Gibco; 1 ml). Then, PI 2-hydroxy-1-(4-(hydroxyethoxy)phenyl)-2-methyl-1-propanone (0.5%, w/v, Irgacure 2959; CIBA Chemicals) was added to the prepolymer solution. A 40 μl droplet of GelMA prepolymer solution was pipetted onto the backside of 80×15 mm$^2$ Pyrex reusable Petri dish (Fisher Scientific) between spacers (cover slip 25×25 mm$^2$, thickness: 150 μm). A photomask (1×1 mm$^2$; square) was set on the coverslip between the UV light and prepolymer droplet, after another coverslip was placed onto the droplet. Microgels were fabricated by applying UV light (2.9 W cm$^{-2}$; at a height of 50 mm above the microgels) for 30 s. Then, photomask and coverslip were removed, and square GelMA microgels were formed on the coverslip. By using a razor, the microgels were transferred into PBS filled assembly chambers.

For the fabrication of radicalized PEGDMA hydrogel building blocks for EPR measurements, a coverslip was placed under poly(methyl methacrylate) (PMMA) mold (PMMA; 1.5 mm height; 3×3 cm$^2$, square) with a cavern (3 mm diameter; circular) in the centre. Then, cylindrical PEGDMA gel was fabricated by filling PEGDMA prepolymer solution (PEGDMA 1000 with 1% PI; and two cases: 20 and 50% (w/v) dissolved into PBS) into the mold. Then, another coverslip was placed onto PMMA mold. UV light (6.9 W cm$^{-2}$; at a height of 50 mm above the mold) was applied for 30 s. Stable radical 4-Amino-2,2,6,6-Tetramethylpiperidine-1-oxyl (4-Amino-Tempo; Sigma; 10 mg; 30 mg ml$^{-1}$; 150 mg) solution was prepared by dissolving stable radical powder into PBS (Gibco; 1 ml). Then, after coverslips were removed, solid cylindrical PEGDMA gel was obtained. Stable radical solution (10, 30, 150 mg dissolved into 1 ml PBS). Then, four cylinder PEGDMA hydrogels were separated into control and experimental groups by following experiments: (i) Control: place a PEGDMA hydrogel into a 35×10 mm$^2$ Pyrex reusable Petri dish (Fisher Scientific) filled with 1 ml PBS for 10 h, (ii) Experiment A: place a PEGDMA hydrogel into a Petri dish filled with 10 mg ml$^{-1}$ stable radical solution for 10 h, (iii) Experiment B: place a PEGDMA hydrogel into a Petri dish filled with 30 mg ml$^{-1}$ stable radical solution for 10 h, (iv) Experiment C: place a PEGDMA hydrogel into a Petri dish filled with 150 mg ml$^{-1}$ stable radical solution for 10 h. Four PEGDMA hydrogels were then placed into the tubes for EPR measurements. Please note that here and in the next sections, 10 h refer to overnight incubation.

For the fabrication of vitamin E-treated PEGDMA hydrogel building blocks for EPR, a coverslip was placed under PMMA mold (1.5 mm height; 3×3 cm$^2$, square) with a cavern (3 mm diameter; circular) in the centre. Cylindrical PEGDMA gel was fabricated by filling PEGDMA prepolymer solution (PEGDMA 1000 with 1% PI; 50% (w/v) dissolved into PBS) into the mold. Then, another coverslip was placed onto PMMA mold. UV light (6.9 W cm$^{-2}$; at a height of 50 mm above the mold) was applied for 30 s to achieve cross-linking within photocross-linkable PEGDMA prepolymer solution. After coverslips were removed, solid cylindrical PEGDMA gel was obtained. Stable radical (4-Amino-Tempo; Sigma) solution (10, 30, 150 mg dissolved into 1 ml PBS). PEGDMA hydrogels were separated into control and experimental groups: (i) Experiment: place a PEGDMA hydrogel into a 35×10 mm$^2$ Pyrex reusable Petri dish (Fisher Scientific) filled with 150 mg ml$^{-1}$ stable radical for 10 h. Then, PEGDMA hydrogel was taken out, washed with 1 ml PBS for three times and soaked into 0.05% (w/v) water soluble vitamin E ((+)-α-Tocopherol acetate; Sigma) dissolved in PBS (Sigma) for another 10 h. (ii) Control A: place a PEGDMA hydrogel into Petri dish filled with 150 mg ml$^{-1}$ stable radical solution for 10 h. (iii) Control B: place a PEGDMA hydrogel into a 35×10 mm$^2$ Petri dish filled with PBS for 10 h.

For PEGDMA gel assemblies, media for paramagnetic floating of hydrogels was prepared by using 20% (v/v) OptiPrep (OptiPrep Density Gradient Medium; Sigma; blending with PBS). Then, 0.001% (v/v) Tween-80 (Tween 80 viscous liquid; Sigma) was added into the solution. For GelMA hydrogel assemblies, media for paramagnetic floating of hydrogels was prepared by using 30% (v/v) OptiPrep (OptiPrep Density Gradient Medium; SIGMA; blending with PBS). Then, 0.001% (v/v) Tween-80 (Tween 80 viscous liquid; SIGMA) was added into the solution.

For cell viability and proliferation assays, NIH 3T3 cells were cultured in Dulbecco's modified Eagle's medium (Invitrogen) supplemented with 10% fetal bovine serum (Invitrogen) and 1% penicillin-streptomycin (Gibco) mixture in a humidified and 5% CO2 containing atmosphere at 37° C.

For MTT (Mw=414) viability assay (Invitrogen), cells were seeded in a 96-well plate with the density of 10$^5$ cells per ml (a total volume of 100 μl cell suspension per well). Stable radical 4-Amino-TEMPO solutions were prepared with the concentrations of 10, 30, 90 and 150 mg ml$^{-1}$. When the cells were attached after 4 h, stable radical solutions were added to the wells in different amounts (1, 2, 5, 10 and 20% (v/v)). The cells were incubated with stable radical solution for 30 min at 37° C. After 30 min, stable radical containing cell culture medium was aspirated from the wells for all samples. Positive control samples were the samples that were not incubated with stable radical. Then fresh culture medium and MTT reagent (10% (v/v)) were added to all wells and incubated for 2 h. At the end of 2 h, resulting formazan was dissolved in 100 μl MTT solubilizing reagent SDS (Mw=288). Absorbance of induced formazan dye was measured by BMG FLUOstar Galaxy—Multifunctional Microplate Reader on the next day. All determinations were carried out in six repeats for each sample and three independent experiments were carried out. MTT proliferation assays were performed 0, 1, 3, 5 and 7 days after the addition of the 4-Amino-TEMPO solution on the cells.

To recover the potential negative effects of stable radicals on cells, vitamin E treatment was performed. Vitamin E solution in sterile PBS was prepared with the maximum solubility of 0.5 mg ml$^{-1}$. Following stable radical incubation, vitamin E solution was added to the wells in different volume ratios as such 1, 5, 10 and 50% (v/v) and cells were incubated for 30 min. After 30 min, vitamin E containing culture medium was aspirated and MTT assay was performed.

Another vitamin E treatment was performed by adding 100% (v/v) vitamin E solution to the wells for 30 min after stable radical incubation. The effect of vitamin E treatment on the viability of 3T3 cells was analyzed by MTT assay for days 0, 1, 3, 5 and 7.

For 3T3 cell encapsulation and live/dead assay, the cover slides used for microgel fabrication were coated with 3-(trimethoxysilyl)propyl methacrylate (TMSPMA, Sigma) as previously described. The secondary coating was applied on the cover slides with 20% (w/v) PEGDMA (2% (w/v) PI). GelMA 5% (w/v) prepolymer solution was prepared by first dissolving the 0.5% (w/v) PI in PBS. When the PI was dissolved completely, lyophilized gelatin methacrylate 5% (w/v) was added and dissolved at 80° C. 3T3 cells were resuspended in prepolymer solution at room temperature (RT) with a cell density of 5×10$^6$ cells per ml right before the encapsulation step. 40 μl of cell suspension in prepolymer solution was placed on a TMSPMA and PEGDMA-coated glass slide and photo-cross-linking was performed under UV light 2.6 mW cm$^{-2}$ for 25 s (Omnicure S2000). 1×1 mm$^2$ cell encapsulating hydrogels were obtained. Cell-laden hydrogels were washed with PBS to remove any remaining prepolymer solution and submerged in culture media and cultured in an incubator (5% CO2, 37° C.) for 4 h. Following the 4 h incubation time, cells were incubated with 30 mg ml$^{-1}$ 5% (v/v) stable radical solution for 30 min and washed. Live/Dead viability assay (Molecular Probes, Invitrogen) was performed for Day 0 samples. Culture media was removed and 150 μl of Live/Dead assay reagent was added to the surface of the microgels and incubated for 20 min at 37° C. Live/Dead dyes were prepared by adding 20 μl of the supplied 2 mM Ethidium homodimer-1 (EthD-1, Molecular Probes) stock solution to 10 ml sterile PBS and vortexed. Then 5 μl of the supplied 4 mM calcein AM stock solution was combined with EthD-1 solution and vortexed again. The living encapsulated cells were labeled green with Calcein AM and the dead cells were labeled red with EthD-1 linker. The florescent images were taken using an inverted fluorescent microscope (Carl-Zeiss AXIO). The viability of the encapsulated cells was quantified with Image J ITCN (Image based tool for counting nuclei) cell counting plug-in.

For immunocytochemistry staining, 3T3 cells encapsulating gels were fixed with 4% paraformaldehyde for 20 min at RT and washed. Gels were permeabilized with 0.3% Triton-X 100 (Sigma), in 1% bovine serum albumin (BSA) (Sigma), for min 2 h at RT. Gels were stained with rabbit anti Ki67 (Ab16667, Abcam) overnight at 4° C. Following the washing step gels were incubated with secondary antibody goat anti-rabbit Alexa Fluor 564 (A11011, Invitrogen) for 2 h at RT. DAPI was used as nuclear counter staining. After washing, hydrogels were visualized under fluorescent microscope (Carl-Zeiss AXIO).

For rat heart dissection and cardiomyocyte isolation, complete growth medium consisted of Dulbecco's modified Eagle's medium (Gibco), 10% horse serum (Gibco), 2.5% fetal bovine serum (Gibco), 100 U ml$^{-1}$ penicillin and 100 mg ml$^{-1}$ streptomycin (Gibco). 0.1% (w/v) collagenase type II enzyme (270 U mg$^{-1}$, Worthington Biochemical) was used to dissociate pieces of heart tissue into single cells. One- to two-day old Sprague-Dawley rats were used for isolation of neonatal cardiomyocytes. Rats were dissected according to the Institutional Animal Care and Use Committee at the Harvard Medical School, under an approved protocol #04821. Hearts were rinsed in ice-cold Hank's Balanced Salt Solution (HBSS) buffer ($Ca^{2+}$- and $Mg^{2+}$-free, Corning Cellgro) to remove blood cell components. They were minced with scissors into 1-2 $mm^3$ pieces into ice-cold HBSS. The minced ventricles were placed in 0.1% (w/v) purified trypsin (Gibco) in ice-cold HBSS for 15-18 h at 4° C. at low-speed shaker. Complete growth medium was added to inhibit trypsin digestion and waited at 37° C. for 5 min. Pieces of heart tissue were incubated with collagenase solution for digestion at 37° C. Incubations were done with collagenase five times (10 min each) and first cell suspension was aspirated to remove dead and damaged cells, debris and blood cells. The collected cell suspensions were passed through a 70 µm cell strainer. Cells were centrifuged at 1,000 r.p.m. for 5 min to remove collagenase. After resuspension in warm complete growth medium, cells were pre-plated for 60 min to enrich cardiac myocytes. After counting cells, the cell suspension was adjusted to a concentration of $1 \times 10^6$ cells in 1 ml GELMA prepolymer solution.

For cardiac cell encapsulation, TMSPMA and 20% (w/v) PEGDMA-coated glass slides were prepared before the cardiomyocyte encapsulation and microgel fabrication. GelMA 3% (w/v) prepolymer solution was prepared by first dissolving the PI 0.1% (w/v) in PBS. When the PI is dissolved completely, lyophilized gelatin methacrylate 3% (w/v) was added and dissolved at 80° C. Primary cardiomyocytes were counted and then resuspended in GelMA 3% (w/v) prepolymer solution with a cell density of $10 \times 10^6$ cells per ml right before the encapsulation step. 40 µl of cell suspension in prepolymer solution was placed on a TMSPMA and PEGDMA-coated glass slide and photocross-linking was performed under UV light 2.9 mW cm$^{-2}$ for 25 s (Omnicure S2000). 1×1 $mm^2$ cell encapsulating hydrogels were obtained by UV photo mask. Cell-laden hydrogels were washed with PBS to remove any remaining prepolymer solution and submerged in culture media then cultured in an incubator (5% $CO_2$, 37° C.) for 4 h. Following the 4 h incubation time, cells were incubated with 10 and 30 mg ml$^{-1}$ 5% (v/v) stable radical 4-Amino-TEMPO solution for 30 min and then washed.

For vitamin E treatment, following stable radical incubation, 0.5 mg ml$^{-1}$ vitamin E solution in culture medium was added to the wells in a concentration of 100% (v/v) and then incubated for 30 min. After 30 min, vitamin E containing culture medium was aspirated and encapsulated cells were further cultured for 10 days.

For immunocytochemistry staining, cardiomyocyte encapsulating hydrogels were fixed with 4% paraformaldehyde for 20 min at RT and washed with PBS. Gels were blocked in 1% BSA (Sigma) and permeabilized with 0.3% Triton-X 100 (Sigma) for min 2 h at RT. Cells were stained with mouse anti-α-actinin (sarcomeric; A7811, Sigma) and rabbit anti-GATA-4 (ab5245, Abcam) for overnight at 4° C. Samples were washed and stained for secondary goat anti-mouse Alexa Fluor 488 and goat anti-rabbit Alexa Fluor 568 antibodies (Life Technologies) for 2 h at RT. Actin cytoskeleton was visualized with Alexa Fluor 647 phalloidin (Life Technologies) and DAPI was used as nuclear counter staining. After washing, hydrogels were visualized with Leica SP8 X inverted confocal microscope (Leica).

For gel fabrication for levitation experiments, Pyrolytic graphite-embedded PEGDMA hydrogel was prepared by adding 90% (w/v) pyrolytic graphite powder into 20% (w/v) PEGDMA prepolymer solution, and vortexing for 1 min. The prepolymer solution was pipetted onto 1×1 $cm^2$ shape PMMA mold laid on a glass coverslip. Another coverslip was then placed upon the mold. The setup was exposed to UV light with optimized parameters: 5 cm between the setup and the light source, 6.9 W cm$^{-2}$ UV intensity and 30 s cross-linking time. The gel was then placed into a PMMA chamber fabricated by laser cutter (VersaLaser, Scottsdale Ariz.) and assembled by epoxy (2 Ton, Clear Epoxy, In DevTube). PBS mixed with OptiPrep was prepared as a pre-solution of paramagnetic medium. 300 mg ml$^{-1}$ stable radical was then added to the pre-solution, forming 1.8 M radical solution to provide a levitation environment for gels.

In another example, two pyrolytic graphite-embedded square PEGDMA gels were fabricated. Two 1×1 $cm^2$ gels were incubated separately in 0.6 M (the gel at left) and 6 M radical solution (gel at right) for overnight. After magnetization, the gels were picked up and place within 0.16 M Gd solution in PMMA chamber for the levitation. The Gd solution was prepared by adding gadolinium salt into PBS, vortexing for 1 min, and then incubated in 80° C. oven for 20 min.

In yet another example, pyrolytic graphite-embedded PEGDMA hydrogel was prepared by adding 90% (w/v) pyrolytic graphite powder, into 20% (w/v) PEGDMA prepolymer solution and vortexed for 1 min. The mixed prepolymer solution was then pipetted onto a 600-µm spacer, and then covered by a coverslip. A photomask (1×1 mm square shape) was placed onto the coverslip. The whole setup was exposed to the UV light with optimized parameters: 5 cm between the setup and the light source, 6.9 W cm$^{-2}$ UV intensity, and 25 s cross-linking time. Individual square PEGDMA gel blocked was picked up. Ten of the gels were stained with blue color and incubated in 6 M radical solution, whereas another ten gels were stained in yellow and incubated in 0.6 M radical solution. In both cases, the gels were incubated overnight. After magnetization, gels were placed within 0.191 M Gd solution in PMMA chamber for the levitation. The Gd solution was prepared by adding gadolinium salt into PBS, vortexing for 1 min and then incubated in 80° C. oven for 20 min.

For hydrogel staining, following fabrication of hydrogels, 1% (w/v) dye (Procion, Mx dye) solution was pipetted on top of hydrogels. After 30 min, cover slips with hydrogels were gently washed twice with PBS. The dye is composed of small molecules and has a minor interaction with the polymer. The dye demonstrated enough interaction to stay for sufficiently long time in the hydrogel for the assembly process.

For radicalized GelMA hydrogel fabrication for EPR measurements, a cover slip was placed under PMMA mold (1.5 mm height; 3 cm×3 cm square) with a cavern (3 mm diameter; circular) in the center. Cylindrical GelMA gel was fabricated by filling GelMA prepolymer solution (5% w/v; dissolved into PBS) into the mold. Another cover slip was then placed onto PMMA mold. UV light (6.9 W/cm2; at a height of 50 mm above the mold) was applied for 30 seconds to achieve cross-linking within photocross-linkable GelMA prepolymer solution. After cover slips were removed, solid cylindrical PEGDMA gel was obtained. Stable radical (4-Amino-Tempo; SIGMA) solution (10 mg; 30 mg; 150 mg dissolved into 1 ml PBS) was prepared. Then, four cylinder GelMA hydrogels were separated into control and experimental groups: (i) Control: Place a GelMA hydrogel into a 35 mm×10 mm Pyrex reusable Petri dish (Fisher Scientific) filled with 1 ml PBS for 10 hours, (ii) Experimental A: Place a GelMA hydrogel into a Petri dish filled with 10 mg/ml stable radical solution for 10 hours, (iii) Experimental B: Place a GelMA hydrogel into a Petri dish filled with 30 mg/ml stable radical solution for 10 hours, (iv) Experimental C: Place a GelMA hydrogel into a Petri dish filled with 150 mg/ml stable radical solution for 10 hours. Four GelMA hydrogels were then placed into the tubes for electron paramagnetic resonance (EPR) measurements.

For mold fabrication for gels for EPR, the mold for cylindrical gels was designed and fabricated by laser cutter (VersaLaser™, Scottsdale Ariz.). PMMA (1.5 mm height; 3 cm×3 cm square) was cut by laser cutter, forming 3 mm diameter cylindrical cavern in the center.

The mold for square gels was designed and fabricated by laser cutter (VersaLaser™, Scottsdale Ariz.). PMMA (1.5 mm height; 2 cm×2 cm square) was cut by laser cutter, forming 1 $cm^2$ square cavern in the center.

For fabrication of chambers for paramagnetic assemblies, all chambers with different shapes and channels were constructed with two layers of 3 mm PMMA and one layer of 150 μm thick double-sided adhesive (DSA), cut by laser cutter (VersaLaser™, Scottsdale Ariz.). Chambers and channels were filled with 20% v/v OptiPrep dissolved in PBS and 0.001% v/v Tween 80 solution. Stained and radicalized hydrogels were assembled one-by-one to form different configurations by Neodymium magnets (1.2×2.4 cm, K&J Magnetics, CA) placed above the gels. The celtic-shaped chamber was composed of three circular reservoirs connected to rectangular channel. The swirl-shaped chamber was composed of four circular reservoirs connected to square channel in the center. The claw-shaped chamber was composed of three circular reservoirs converged to rectangular channel on the left. The tree branches-shaped chamber was composed of five circular reservoirs converged to rectangular channel on the left.

For fabrication of glass bubble encapsulating lighter gels, 50% w/v glass bubbles (3M™, Glass Bubbles S38HS) were added into 50% w/v PEGDMA prepolymer solution (with 1% w/v photoinitiator (PI), Irgacure 2959; CIBA Chemicals). 40 PEGDMA prepolymer solution was pipetted to spacers (cover slip 25×25 $mm^2$, thickness: 150 μm) on the backside of 95 mm×15 mm Pyrex reusable Petri dish (Fisher Scientific). Another cover slip was placed onto the droplet. A photomask (1 mm×1 mm; square) was set on the cover slip between the UV light and prepolymer droplet. Microgels were fabricated by applying UV light (2.9 W/$cm^2$; at a height of 50 mm above the microgels) for 20 seconds. Then, photomask and cover slip were removed, and square, ivory colored PEGDMA microgels were formed.

To evaluate the effect of heterogeneous porosity on the mechanical properties of the hydrogel, compression tests were performed by using ADMET eXpert 2600 dual column testing machines (Norwood, Mass., USA). Six samples of each case below were prepared for the mechanical test:

For fabrication of macro-porous PEGDMA gel, 90% (w/v) sucrose embedded PEGDMA prepolymer solution including 2% (w/v) PI was poured onto a 300 μm thick DSA mold (cavities shape) laid between two cover slips. The setup was exposed to UV light (360-480 nm) under the optimized parameters: 5 cm height between the light source and the setup, 6.9 W/$cm^2$ intensity, and 40 seconds cross-linking time. Then, the gels were all immersed within PBS, which was changed by every 10 minutes during 2 hours. After sucrose was leached out and macro-porous PEGDMA gels were formed (4.5 mm width of its cross section area), the gels were then stained by food dye for 1 hour.

For fabrication of nano-porous PEGDMA gel, 1% (w/v) PI was added into 50% (w/v) PEGDMA prepolymer solution. Then, 80 μl prepolymer solution was pipetted onto a 300 μm thick spacer, and covered by a cover slip. Circular-shaped photomask was placed upon the cover slip. The whole set up was exposed to UV light (360-480 nm) under the optimized parameters: 5 cm height between the light source and the setup, 6.9 W/$cm^2$ intensity, and 30 seconds cross-linking time. The circular-shaped gels (1 mm width of its cross section area) were then stained by food dye for 1 hour.

For fabrication of composite gel, both macroporous and nanoporous PEGDMA gels were kept in 30 mg/ml 4-AMINO-TEMPO solution for 30 minutes after the staining. Neodymium magnet was used to assemble an X-shape, macro-porous PEGDMA gel with four circular 50% (w/v) nano-porous PEGDMA gels. After the assembly process, the swimming solution was pipetted out very slowly (300 μl at a time, preventing potential disassembly of gels), until the assembled gels were settled down to the bottom of the reservoir. 40 μl, 50% (w/v) PEGDMA prepolymer solution was pipetted onto the assembled gels, and second-cross-linking was performed. The cross-linked gels were covered by 10 ml PBS as the first layer, then with another 10 ml of mineral oil (Sigma-Aldrich) as a second layer. The same assembly was repeated at the same area above the previous assembly. The mineral oil and PBS liquid layers were then carefully pipetted out until the assemblies stacked together. 40 μl, 50% (w/v) PEGDMA prepolymer solution was added to the assembled gels, which was placed onto a 600 μm spacer. Then, another cross-linking was performed. After the residuals were removed, the composite gel was cut into a rectangular shape (4.5 mm width of its cross section area).

All hydrogel samples were compressed at a rate of 0.2 mm/min until failure occurred. The Young's modulus was determined as the slope of the initial linear region of the compressive stress-strain curve in the first 5-20% strain range.

For average velocity measurement for single magnetized hydrogel for a range of distances between gel and magnet, 20% (w/v) PEGDMA prepolymer solution was prepared. Then, 1% (w/v) PI was added to the prepolymer solution. The mixed solution was incubated within 80° C. oven for 20-30 minutes, until PEGDMA and PI were well dissolved. 200 μl prepared prepolymer solution was pipetted onto a 600 μm-thick spacer, and a cover slip was placed upon prepolymer solution, forming a sandwich-like setup. The whole setup was exposed to 2.6 W/$cm^2$ UV for 30 seconds. A 1 mm×1 mm square shape photomask was used for tuning the shape of hydrogels. After gelation, hydrogel slide was incubated within 1.2 M (200 mg/ml) 4-AMINO-TEMPO solution for 30 minutes. Then, washing the slide with PBS for 3 times, and staining the slide with red food dye (Procion® MX Dye, 030 Fire Engine Red) for 1 hour. A magnetized, stained small hydrogel building block was picked up and placed upon a medium mixed with OptiPrep and PBS. The preparation of medium for maintaining the gel upon surface was achieved by adding 20% (v/v) OptiPrep to 80% (v/v) PBS. The setup using for the experiment was fabricated by 3 mm thick PMMA, which was to fix the permanent magnet. The distance between the bottom surface of the magnet and petri-dish was set as 1 cm. 8.5 cm diameter; circular-shaped petri dish was used. Three different vertical distances: 1, 2, and 3 mm were set between magnet and hydrogel. 1 mm height (0.9 cm height of the total medium) controlled by filling 51.04 ml medium to the petri dish. 2 mm height (0.8 cm height of the total medium) controlled by filling 45.37 ml medium to the petri dish. 3 mm height (0.7 cm height of the total medium) controlled by filling 39.7 ml medium to the petri dish. For each experiment, a hydrogel was placed at 1.5 cm distance (measured from the center of magnet). After the magnet was inserted (and fixed), magnetized hydrogel started to move towards the magnet gradually due to its paramagnetic property. By recording the process, average velocities were obtained. After 6 repeats, traveling time was obtained (t=0 when magnet was fixed) and average velocity and its standard deviation was calculated and then plotted into chart.

For measuring average velocity of Vitamin E-treated magnetized hydrogel, 20% (w/v) PEGDMA prepolymer solution was prepared. Then, 1% (w/v) PI was added to the prepolymer solution. The mixed solution was incubated within 80° C. oven for 20-30 minutes, until PEGDMA and PI were well dissolved. 200 µl prepared prepolymer solution was pipetted onto a 600 µm-thick spacer, and a cover slip was placed upon prepolymer solution, forming a sandwich-like setup. The whole setup was exposed to 2.6 W/cm² UV for 30 seconds. A 1 mm×1 mm square shape photomask was used for tuning the shape of hydrogels. After gelation, hydrogel slide was incubated within 1.2 M (200 mg/ml) 4-AMINO-TEMPO solution for 30 minutes. Then, washing the slide with PBS for 3 times, and staining the slide with red food dye (Procion MX Dye, 030 Fire Engine Red) for 1 hour. Differently from the velocity analysis of previous experiment, 0.5 mg/ml Vitamin E was pipetted onto the gel slides after staining for 30 minutes, 1 hour and 2 hours (3 slides total), to investigate the effect of Vitamin E on free radical. After Vitamin E treatment, a hydrogel building block was placed upon a medium mixed with OptiPrep and PBS. The preparation of medium for maintaining the gel upon surface was achieved by adding 20% (v/v) OptiPrep to 80% (v/v) PBS. The distance between the magnet and the surface of medium was set to 1 mm. For each experiment, a hydrogel was placed at 1.5 cm distance (measured from the center of magnet). After 6 repeats, traveling time was obtained (t=0 when magnet was fixed) and average velocity and its standard deviation were calculated and then plotted into chart. For the levitation of beads in radical solution, chambers of 1.5, 2.6 and 3.6 cm height were fabricated using 3 mm thick PMMA. 45 polystyrene beads (Chromo-Spheres™ Red Polymer Microspheres) were first placed in OptiPrep solution (OptiPrep™ Density Gradient Medium, SIGMA). Then, we continuously added PBS into the OptiPrep, until all beads were just about to sink toward to the bottom. 1.8 M (300 mg/ml) stable radical was added into the solution, well-vortexed and placed within 80° C. oven for 30 minutes, until 4-AMINO-TEMPO was dissolved within the solution. The beads and 4-AMINO-TEMPO solution was then pipetted to different height of PMMA chamber (45 beads in each chamber). Then, reservoirs were placed into the magnetic device and bead motions were recorded. Assembly area, defined as the rectangle area encased by the lines passing through the most outer beads, were calculated after image analysis. For 1.5 cm height chamber, assembled areas were calculated at t=0, 15, 30, 45, 60, 105, 135, 165 and 180 seconds. For 2.6 cm height chamber, assembled areas were calculated at t=0, 30, 70, 100, 130, 150, 190, 220, 250 and 300 seconds. For 3.6 cm height chamber, assembled areas were calculated at t=0, 30, 55, 75, 100, 120, 150, 180, 240, 270, 300, 330, 360 seconds (t=0 when the chamber was fixed between magnets).

The present invention has been described in terms of one or more preferred embodiments, and it should be appreciated that many equivalents, alternatives, variations, and modifications, aside from those expressly stated, are possible and within the scope of the invention. For example, in some embodiments, stable radicals may have a known half life such that the radical form of the molecule decays over time to a neutral, non-radical form. Accordingly, it may be possible to select radical molecules that are active during assembly and then are neutralized shortly thereafter due to natural decay. In such an example, it may be possible to forgo the use of an antioxidant treatment step.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A method for self-assembly of magnetic building blocks, the method comprising:
    distributing a plurality of building blocks in a liquid medium, each of the plurality of building blocks comprising a plurality of stable radicals;
    establishing a magnetic field interacting with at least a portion of the plurality of building blocks;
    guiding with the magnetic field the portion of the plurality of building blocks from a first location in the liquid medium to a second location in the liquid medium;
    assembling into a first construct the portion of the plurality of building blocks proximate the second location; and
    treating the first construct with at least one antioxidant to neutralize at least in part the plurality of stable radicals.

2. The method of claim 1, further including incubating the plurality of building blocks in a composition comprising the plurality of stable radicals.

3. The method of claim 1, wherein the step of assembling into the construct the portion of the plurality of building blocks further including cross-linking together each of the building blocks that comprise the first construct.

4. The method of claim 1, wherein the plurality of building blocks comprises at least one of nucleic acids, proteins, cells, and tissues.

5. The method of claim 1, wherein the plurality of building blocks is essentially free of iron, nickel, and cobalt.

6. The method of claim 1, wherein the density of each of the plurality of building blocks is less than the density of the liquid medium such that the plurality of building blocks floats on a surface of the liquid medium.

7. The method of claim 1, wherein the plurality of building blocks includes at least a first fraction of building blocks having a first density and a second fraction of building blocks having a second density different from the first density such that there is a differential in buoyancy between the first fraction and the second fraction.

8. The method of claim 1, further including:
submerging the first construct in a first liquid phase;
forming a second liquid phase on top of the first liquid phase;
assembling a second construct comprising at least a second portion of the plurality of building blocks, the second construct assembled in the second liquid phase relatively above the first construct; and
displacing at least one of the first liquid phase and the second liquid phase, thereby layering the second construct on the first construct to form a three dimensional structure.

9. The method of claim 1, wherein the liquid medium includes a surfactant to decrease the surface tension and drag forces on the plurality of building blocks.

10. The method of claim 1, wherein the plurality of building blocks comprising the plurality of stable radicals is paramagnetic.

11. A system for self-assembly of magnetic building blocks, the system comprising:
a liquid medium;
a reservoir for containing the liquid medium;
a plurality of building blocks for distribution in the liquid medium, each of the plurality of building blocks comprising a plurality of stable radicals;
a magnetic field established relative to the reservoir, the magnetic field interacting with at least a portion plurality of building blocks when the plurality of building blocks are distributed in the liquid medium, the magnetic field operable to guide the portion of the plurality of building blocks from a first location in the liquid medium to a second location in the liquid medium and assemble into a first construct the portion of the plurality of building blocks proximate the second location; and
a composition comprising an antioxidant for treating the first construct to neutralize at least in part the plurality of stable radicals.

12. The system of claim 11, wherein the liquid medium includes a surfactant to decrease the surface tension and drag forces on the plurality of building blocks.

13. The system of claim 11, wherein the plurality of building blocks comprises at least one of nucleic acids, proteins, cells, and tissues.

14. The system of claim 11, wherein the plurality of building blocks is essentially free of iron, nickel, and cobalt.

15. The system of claim 11, wherein the density of each of the plurality of building blocks is less than the density of the liquid medium such that the plurality of building blocks floats on a surface of the liquid medium.

16. The system of claim 11, wherein the plurality of building blocks includes at least a first fraction of building blocks having a first density and a second fraction of building blocks having a second density different from the first density such that there is a differential in buoyancy between the first fraction and the second fraction.

17. The system of claim 11, further including a permanent magnet for establishing the magnetic field.

18. The system of claim 11, wherein the plurality of building blocks comprising the plurality of stable radicals is paramagnetic.

19. The system of claim 11, further comprising at least one ultraviolet light source for cross-linking the portion of the plurality of building blocks that comprises the first construct.

20. A method for self-assembly of magnetic building blocks, the method comprising:
incubating a plurality of building blocks in a composition comprising a plurality of stable radicals;
distributing the plurality of building blocks in a reservoir containing a liquid medium;
establishing a magnetic field with a permanent magnet, the magnetic field encompassing at least a portion of the plurality of building blocks;
guiding with the magnetic field the portion of the plurality of building blocks from a first location in the liquid medium to a second location in the liquid medium;
assembling into a first construct the portion of the plurality of building blocks proximate the second location;
cross-linking the portion of the plurality of building blocks that comprises the first construct; and
treating the first construct with at least one antioxidant to neutralize at least in part the plurality of stable radicals;
wherein the density of each of the plurality of building blocks is less than the density of the liquid medium such that the plurality of building blocks floats on a surface of the liquid medium.

* * * * *

UNITED STATES PATENT AND TRADEMARK OFFICE
CERTIFICATE OF CORRECTION

PATENT NO. : 10,208,282 B2
APPLICATION NO. : 15/121635
DATED : February 19, 2019
INVENTOR(S) : Utkan Demirci et al.

Page 1 of 1

It is certified that error appears in the above-identified patent and that said Letters Patent is hereby corrected as shown below:

In the Specification

Column 1, Line 22, "R21HL112114" should be --NIH/HL112114--.

Signed and Sealed this
Twenty-second Day of October, 2024

Katherine Kelly Vidal
*Director of the United States Patent and Trademark Office*